(12) United States Patent
Winquist et al.

(10) Patent No.: US 6,613,049 B2
(45) Date of Patent: Sep. 2, 2003

(54) ADJUSTABLE BONE STABILIZING FRAME SYSTEM

(76) Inventors: Robert A. Winquist, 2311 5th Ave., North, Seattle, WA (US) 98060; Roy Bogert, 19 Francis Rd., Lincoln Park, NJ (US) 07035; Charles Hummel, 21 Maple Dr., North Caldwell, NJ (US) 07006; James Seaton, 16 Fairmount Ave., Chatham, NJ (US) 07928; James Nelson, 19 Davenport Pl., Morristown, NJ (US) 07960

(*) Notice: Subject to any disclaimer, the term of this patent is extended or adjusted under 35 U.S.C. 154(b) by 85 days.

(21) Appl. No.: 09/757,912

(22) Filed: Jan. 10, 2001

(65) Prior Publication Data

US 2002/0165543 A1 Nov. 7, 2002

Related U.S. Application Data

(60) Provisional application No. 60/179,878, filed on Feb. 2, 2000.

(51) Int. Cl.$^7$ ............................................. A61B 17/64
(52) U.S. Cl. ............................. 606/59; 606/55; 606/54
(58) Field of Search ............................. 606/54, 59, 58, 606/65–68, 53, 57, 105; 292/256–258

(56) References Cited

U.S. PATENT DOCUMENTS

| | | | | |
|---|---|---|---|---|
| 4,483,334 A | * | 11/1984 | Murray | 606/59 |
| 5,624,440 A | * | 4/1997 | Huebner | 606/59 |
| 5,630,817 A | * | 5/1997 | Rokegem et al. | 606/61 |
| 5,669,910 A | * | 9/1997 | Korhonen et al. | 606/61 |
| 5,683,389 A | * | 11/1997 | Orsak | 606/59 |
| 5,709,681 A | * | 1/1998 | Pennig | 606/54 |
| 5,728,096 A | * | 3/1998 | Faccioli et al. | 606/54 |
| 5,810,817 A | * | 9/1998 | Roussouly et al. | 606/61 |
| 5,891,144 A | * | 4/1999 | Mata et al. | 606/59 |
| 5,976,134 A | * | 11/1999 | Huebner | 606/59 |
| 6,019,769 A | * | 2/2000 | McCarthy et al. | 606/105 |
| 6,022,348 A | * | 2/2000 | Spitzer | 606/54 |
| 6,171,308 B1 | * | 1/2001 | Bailey et al. | 606/54 |
| 6,235,029 B1 | * | 5/2001 | Faccioli et al. | 606/54 |
| 6,277,118 B1 | * | 8/2001 | Grant et al. | 606/54 |
| 6,277,119 B1 | * | 8/2001 | Walulik et al. | 606/57 |
| 6,340,361 B1 | * | 1/2002 | Kraus et al. | 606/59 |
| 6,342,054 B1 | * | 1/2002 | Mata | 606/59 |
| 6,355,037 B1 | * | 3/2002 | Crosslin et al. | 606/57 |
| 6,491,694 B1 | * | 12/2002 | Orsak | 606/57 |

* cited by examiner

Primary Examiner—Henry Bennett
Assistant Examiner—Kathryn Ferko

(57) ABSTRACT

By providing components securable to anchor pins or screws of different diameters as well as providing clamps which hold associated pins in any position during adjustments, an external fixation or adjustable frame structure is provided which is capable of being quickly and easily assembled in any desired configuration. In the present invention, the frame structure is retained in any assembled configuration in order to allow final adjustments to be made, prior to the final securement of the frame assembly in the precisely desired configuration by closure of each clamp member. In this way, an entire frame assembly is capable of being constructed, adjusted, and readjusted in order to assure each component is oriented in the precisely desired position prior to final closure of the clamping members. In one preferred embodiment, the clamping members employed in the frame structure of the present invention incorporate friction pins internally mounted in each clamp which engages the rod member once this rod is inserted into the jaws of the clamp. In this way, any rod member inserted into the clamping jaws contacts the surface of the jaws and the friction pin, preventing the rod member from sliding or moving relative to the clamp. In addition, by incorporating a uniquely constructed, moving wedge plate that is adjustably engageable with any cooperating anchor pin, secure affixation of the mounting member with the anchor pins of any diameter is easily achieved, regardless of the orientation configuration, or diameter of the anchor pin.

18 Claims, 16 Drawing Sheets

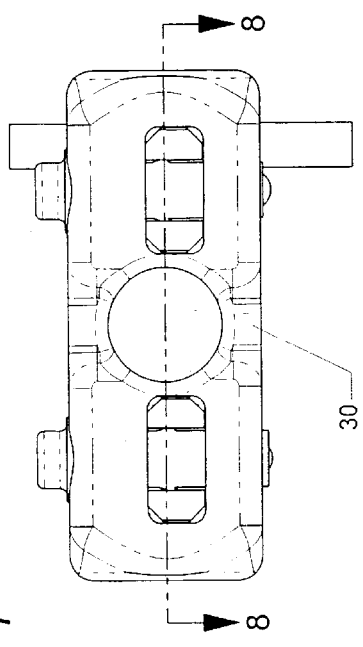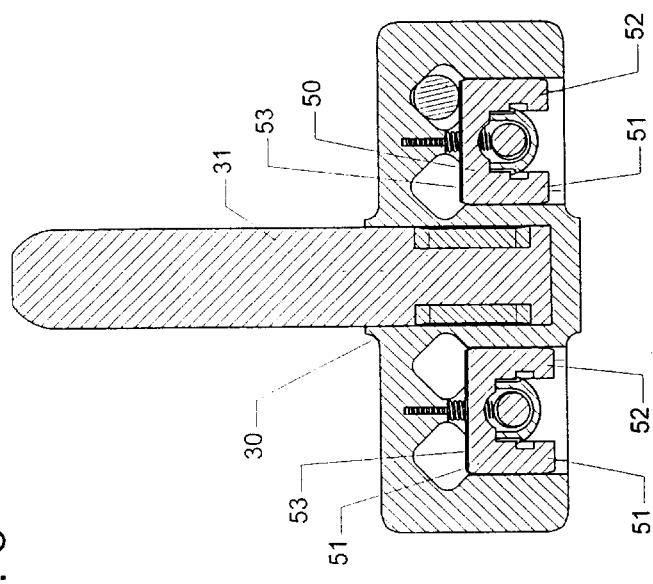
FIG. 7
FIG. 8

ADJUSTABLE BONE STABILIZING FRAME SYSTEM

RELATED APPLICATIONS

This application claims the benefit of U.S. Provisional Application No. 60/179,878 filed Feb. 2, 2000.

This application is related to U.S. Provisional Patent Application Serial No. 60/179,878, filed Feb. 2, 2000 entitled ADJUSTABLE BONE STABILIZING FRAME SYSTEM.

TECHNICAL FIELD

This invention relates to external fixation or adjustable bone stabilizing frame systems and, more particularly, to frame assemblies employed with broken and/or fractured bones for retaining and holding the bone and in a desired configuration for resetting.

BACKGROUND ART

The use of external fixation or stabilizing frames for retaining broken or fractured bones in a particularly desired orientation or configuration is widely known and commonly employed. However, in most typical prior art external frame constructions, particularly frame constructions employed to stabilize broken or fractured bones, a variety of clamps and holding rods are employed to enable the surgeon to position the broken/fractured bones in a precisely desired position or orientation, and then allowing the bone to be retained in that position or orientation for healing.

Although wide variety of frame structures and clamp systems have been used for this purpose, one common problem existing with most prior art stabilizing frame constructions is the inability to allow the frame construction to be easily adjustable during its assembly. In this regard, in most applications, anchor pins or anchor screws are mounted in a fractured bone, extending outwardly therefrom for attachment to a frame assembly. Clamp members are mounted to the anchor pins or anchor screws with a plurality of rod members being mounted to a plurality of interconnecting clamps to establish the desired stabilizing frame assembly. However, during the creation of the frame structure, which must be maintained in a precise orientation in order to assure that the bone fracture is precisely aligned for healing, these prior art frame systems have been found to be incapable of being retained in a desired position unless securely clamped. As a result, repeated tightening and loosening of the clamps is required before the precisely desired frame structure is fully assembled.

In those instances where the frame assembly being created has an insufficient clamping force applied to the rod members for securing the rod members in the clamp, slippage of the rod in the clamp often occurs. This causes the frame structure to become improperly aligned, resulting in repeated efforts to recreate and readjust the frame.

In addition, since improper alignment may cause the bone elements to be dislodged from the desired position or may impose improper forces upon the bone elements, the slippage caused by loose rods cannot be tolerated. As a result, the arduous task of clamping and unclamping every interconnection must be imposed upon the physician, in order to assure a frame structure is created having the precisely desired configuration and orientation and is maintained in that position throughout its assembly.

In an attempt to satisfy this need, some clamp members incorporate coil springs to prevent slippage. However, these systems do not provide the desired result and are expensive to produce.

Therefore, it is a principal object of the present invention to provide an adjustable frame structure for stabilizing broken or fractured bones which is capable of being the easily constructed by attaching two anchoring pins or screws, with all compounds thereof being retained in any desired position, without the application of final clamping forces.

Another object to the present invention is to provide an adjustable frame structure having the characteristic features described above which allows ease of assembly while still assuring secure, clamped interengagement of all components when required.

Another object of the present invention is to provide an adjustable frame structure having the characteristic features described above which automatically incorporates friction engagement between sliding components for maintaining such component in any position without requiring a clamping force.

Other and more specific objects will impart the obvious and will impart appear hereinafter.

SUMMARY OF THE INVENTION

By employing the present invention, all of the difficulties and drawbacks found in the prior art are eliminated and a fully external fixation or adjustable frame structure is provided which is capable of being quickly and easily assembled in any desired configuration. In addition, the frame structure of the present invention is retained in any assembled configuration in order to allow final adjustments to be made, prior to the final securement of the frame assembly in the precisely desired configuration by closure of each clamp member. In this way, an entire frame assembly is capable of being constructed, adjusted, and readjusted in order to assure each component is oriented in the precisely desired position prior to final closure of the clamp being members.

In order to attain this previously unrealized goal, the clamping members employed in the frame structure of the present invention incorporate friction pins internally mounted in each clamp which engages the rod member once this rod is inserted into the jaws of the clamp. In this way, any rod member inserted into the clamping jaws contacts the surface of the jaws and the friction pin. This contact prevents the rod member from sliding or moving relative to the clamp. As a result of this friction engagement, the rod member is retained in any position relative to the clamping jaws, once the rod member has been inserted into the jaws of the clamp.

By employing the present invention, a frame assembly is quickly in easily constructed in the overall desired configuration with every rod member and clamp being retained in the position originally placed. Once the basic frame structure has been created, final adjustments can be easily made by moving the rod members relative to the clamping jaws, with complete assurance that unwanted slippage will not occur. Once the final configuration has been obtained, each clamp is closed to securely engage the jaws of the clamp with the rod member, thereby assuring the creating of an external fixation assembly or frame structure having a precisely desired configuration for imparting the desired beneficial results.

In addition, the external fixation system or frame assembly of the present invention incorporates components capable of being secured to anchor pins or screws having a wide variety of diameters. By incorporating a uniquely constructed, moving wedge plate that is adjustably engageable with any cooperating anchor pin, secure affixation of the mounting member with the anchor pins is easily achieved, regardless of the orientation configuration, or diameter of the anchor pin.

The invention accordingly comprises the features of construction, combination of elements and arrangement of parts which will be exemplified in the constructions hereinafter set forth, and the scope of the invention will be indicated in the claims.

THE DRAWINGS

For a fuller understanding of the nature and objects of the present invention, reference should be had to the following detailed description taken in connection with the accompanying drawings, in which:

FIG. 7 is a rear view of the pin clamping/mounting member of FIG. 4;

FIG. 8 is a cross-sectional plan view of the pin clamping/mounting member taken along line 8—8 of FIG. 7;

DETAILED DISCLOSURE

By referring to FIGS. 1–24 along with the following detailed discussion, the construction and operation of the external fixation or adjustable frame system of the present invention can best be understood. Although the following disclosure fully details different embodiments of the present invention, these embodiments are provided as preferred examples of the present invention. Consequently, it is to be understood that these embodiments are provided for exemplary purposes only, and are not intended as a limitation of the present invention.

Figure 1:
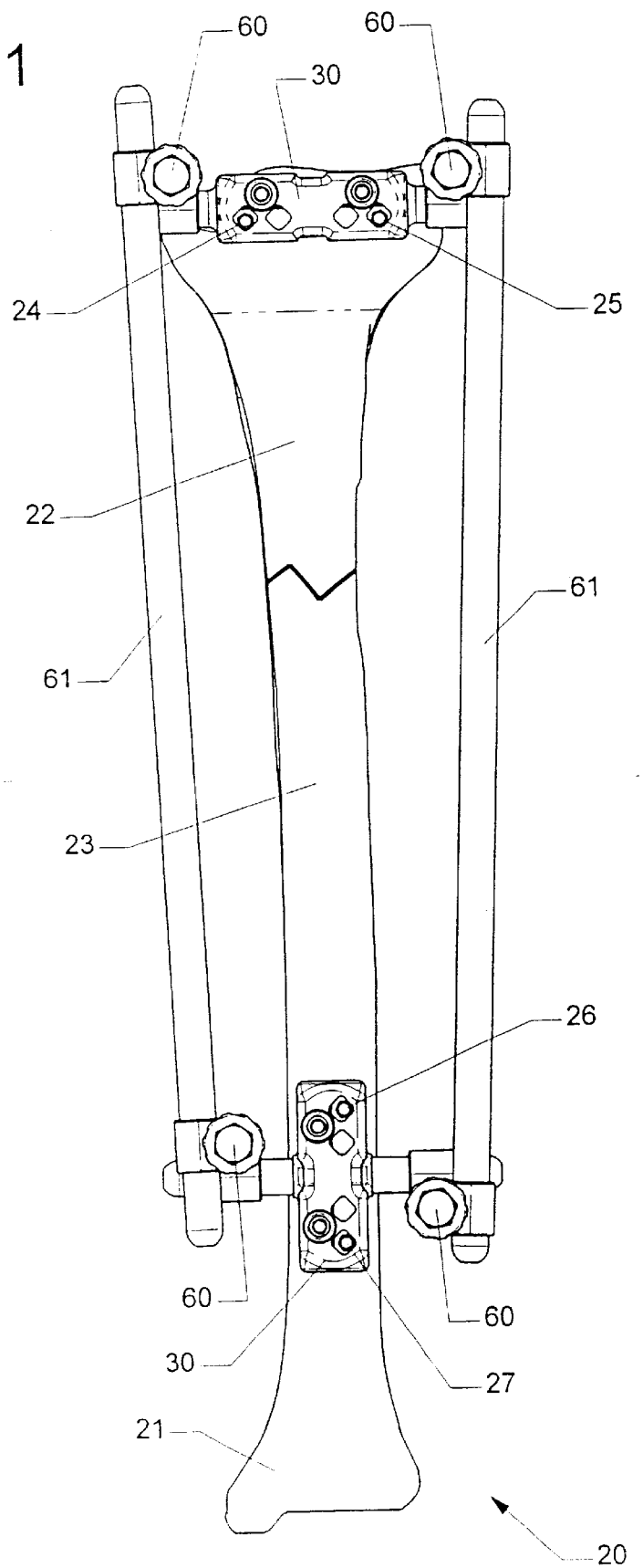
FIG. 1 is a side elevation view depicting one embodiment of a fully assembled external fixation bone stabilizing frame system of the present invention securely mounted for stabilizing a broken tibia.

In FIG. 1, one embodiment of the external fixation or adjustable frame system 20 of the present invention is depicted, securely mounted to broken leg bone 21 or a tibia for maintaining the components of the broken bone in the precisely desired position for healing. As depicted, leg bone 21 has a transverse break, forming upper part 22 and lower part 23.

In order to set and maintain bone 21 in the desired configuration for healing, anchor pins 24 and 25 are mounted in upper part 22, while anchor pins 26 and 27 are mounted in lower part 23. In each instance, the anchor pin is securely affixed to the bone element and extends outwardly therefrom. Using these externally extending anchor pins, frame system 20 is created to form an external fixation frame system which secures and holds parts 22 and 23 of bone 21 in interconnected engagement with each other in order to promote complete healing thereof.

One principal component employed in the external fixation frame system of the present invention is pin clamping and mounting member 30. As is more fully detailed below, pin clamping/mounting member 30 may incorporate one or two connecting rods 31, with one or two connecting rods 31 being mounted at opposite ends or substantially mid-way along the length of mounting member 30. In the embodiments depicted in FIG. 1, mounting member 30 secured to upper part 22 of bone 21 comprises two rods 31 extending from opposite ends thereof, while mounting member 30 affixed to lower part 23 comprises two rods 31 mounted midway along the length of member 30.

Regardless of the position or number of connecting rods 31 mounted to pin clamping/mounting member 30, the overall construction of clamping/mounting member 30 is substantially identical. In order to best understand this construction, reference should be made to FIGS. 2, 3 and 4, wherein these alternate embodiments are depicted, as fully detailed below. In addition, reference should also be made to FIGS. 5–8, wherein details of construction are shown.

In the preferred construction, pin clamping/mounting member 30 incorporates a generally rectangular shaped housing with four separate and independent pin receiving cavities 32, 33, 34, and 35 formed therein, extending from the top surface of the housing to the bottom surface. In addition, as is more fully detailed below, each pin receiving cavity 32, 33, 34, and 35 preferably comprises a generally rectangular or square cross-sectional shape.

Furthermore, a screw receiving cavity 36 is formed adjacent pin-receiving cavities 32 and 33, while screw receiving cavity 37 is formed adjacent pin receiving cavities 34 and 35. In addition, screw receiving cavities 36 and 37, and pin receiving cavities 32, 33, 34, and 35 all extend from the top to the bottom of the housing, with all axes thereof being substantially parallel to each other.

In addition, two elongated slots 38 and 39 are formed in one sidewall of the housing forming pin clamping/mounting member 30. Preferably, each slot 38 and 39 extends into the interior of the housing, through the axes formed by one of the screw receiving cavities and terminating at the axis of the adjacent pin receiving cavities. In this way, slot 38 extends from one side of member 30 through screw receiving cavity 36 and pin receiving cavities 32 and 33 while slot 39 extends from the side wall of member 30 through screw receiving cavity 37 and pin receiving cavities 34 and 35. However, slots 38 and 39 do not extend completely through member 30 to its opposed side wall.

In completing the principal construction of pin clamping/mounting member 30, clamping plates 40 and 41 are employed and constructed for sliding engagement in slots 38 and 39 with locking wedges 42 and 43 controllably engaged with clamping plates 40 and 41. As depicted, clamping plate 40 is inserted in slot 38 for translational movement therein, with locking wedge 42 centrally engaged with plate 40 for moving plate 40 in slot 38. Similarly, clamping plate 41 is inserted in slot 39 for translational movement therein with locking wedge 43 cooperatively associated therewith for controlling the movement of late 41 in slot 39.

Locking wedge 42 is mounted in the base of screw receiving cavity 36 and constructed for being threadedly engaged with movement control screw 44. Similarly, locking wedge 43 is mounted in the base of screw receiving cavity 37 and constructed for threaded engagement with movement control screw 45. By employing this construction, rotation of screws 44 and 45 in a first direction draws locking wedges 42 and 43 into pin clamping/mounting member 30, while rotation of screws 44 and 45 in the opposite direction causes locking wedges 42 and 43 to be forced outwardly from member 30.

In order to provide secure affixation of pin clamping/mounting member 30 with the anchor pins inserted into the bone being stabilized, clamping plates 40 and 41 are preferably constructed within a substantially C-shape, with center portions 50 and legs 51 and 52 extending therefrom. Preferably, the outside wall of center portion 50 incorporates a plurality of longitudinal ribs 53 formed therein and extending substantially parallel to each other.

In addition, a cam slot 54 is formed in the inside wall of legs 51 and 52, with cam slots 54 of each leg being in juxtaposed, spaced, cooperating relationship with each other. Furthermore, cam slots 54 are slanted and positioned for cooperating engagement with camming flanges 55, as detailed below.

In order to control the movement of plates 40 and 41, locking wedges 42 and 43 each comprise camming flanges 55 formed on the outside walls thereof, positioned for cooperative, aligned, controlling engagement with cam slots 54 of each clamping plate 40 and 41. By employing this construction, rotation of screws 44 and 45 in a first direction, which causes wedges 42 and 43 to move into member 30, also causes camming flanges 55 to advance upwardly in cam slots 54, forcing clamping plates 40 and 41 to advance in slots 38 and 39 towards pin receiving cavities 32, 33, 34, and 35. By controlling the slope angle employed in forming cam slots 54 and camming flanges 55, the rate of movement of clamping plates 40 and 41 in slots 38 and 39 is precisely controlled.

Figure 6:
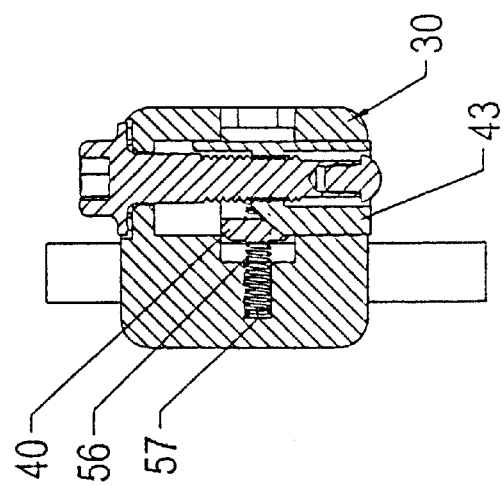
FIG. 6 is a cross-sectional side elevation view taken along line 6—6 of FIG. 5.
Figure 5:
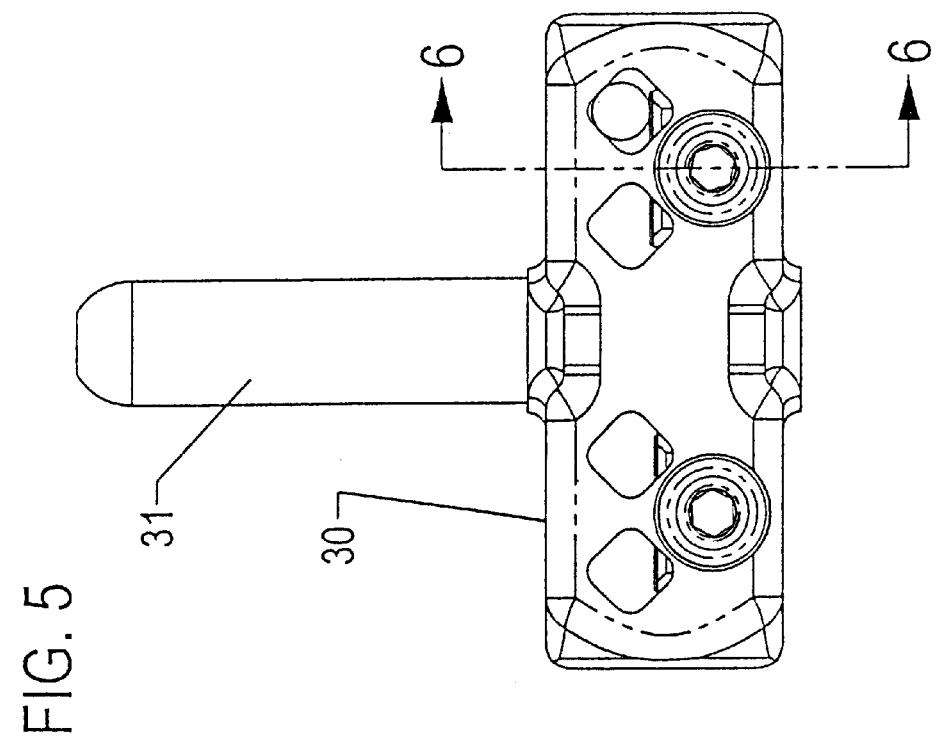
FIG. 5 is a top plan view of the pin clamping/mounting member of FIG. 4.

Furthermore, in the preferred embodiment, spring means 56, in the form of a coil spring, is inserted in slots 38 and 39 in biasing engagement with center portion 50 of clamping plates 40 and 41. Preferably, as shown in FIG. 6, spring means 56 is retained in cavity 57 formed in pin clamping/mounting member 30. In this way, clamping plates 40 and 41 are continuously urged out of pin clamping/mounting member 30 preventing binding of clamping plates 40 and 41 with anchor pin 24 when removal is desired. In addition, spring means 56 continuously biases clamping plates 40 and 41 away from pin receiving cavities 32, 33, 34 and 35, thereby facilitating the easy entry of the desired anchor pins into pin receiving cavities 32, 33, 34, and 35.

By employing the construction detailed above, clamping/mounting member 30 is quickly and easily secured to any desired anchor pins. Using the assembly depicted in FIG. 1, one pin clamping mounting member 30 is mounted to upper part 22 of bone 21 by telescopically advancing pin 24 through cavity 32 or 33, while also advancing pin 25 through cavity 34 or 35. Then, secure affixation of pin clamping /mounting member 30 to anchor pins 24 and 25 is easily achieved by rotationally advancing screws 44 and 45 into member 30, causing locking wedges 42 and 43 to be drawn into member 30.

As detailed above, the upward movement of wedges 42 and 43 causes clamping plates 40 and 41 to be advanced in slots 38 and 39 towards anchor pins 24 and 25. This movement brings the front wall of center portion 50 of plates 40 into contact with pin 24, while the front wall of center portion 50 of plate 41 contacts pin 25. The rotation of screws 44 and 45 continue until pins 24 and 25 are lockingly engaged with plates 40 and 41. By employing ribs 53 on the surface of the front wall of center portion 50, slippage is prevented and secure locked engagement of member 30 with anchor pins 24 and 25 is assured.

Using a virtually identical procedure, pin clamping/mounting member 30 is secured to pins 26 and 27 which are mounted to lower part 23 of bone 21. Once plates 40 and 41 have been advanced into secure, abutting, frictional engagement with anchor pins 26 and 27, as detailed above, member 30 is securely affixed to anchor pins 26 and 27, as well as lower part 23.

Figure 2:
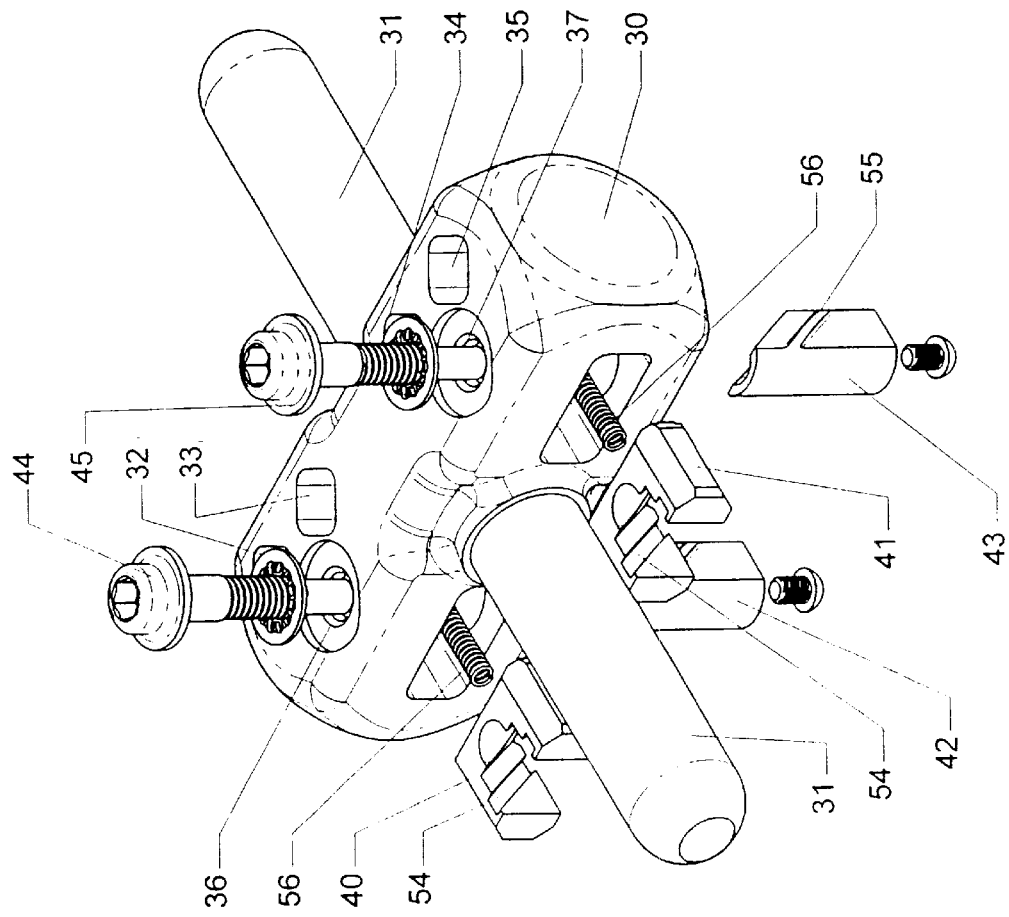
FIG. 2 is a partially exploded perspective view of one embodiment of a pin clamping/mounting member forming one component of the frame system of the present invention.
Figure 3:
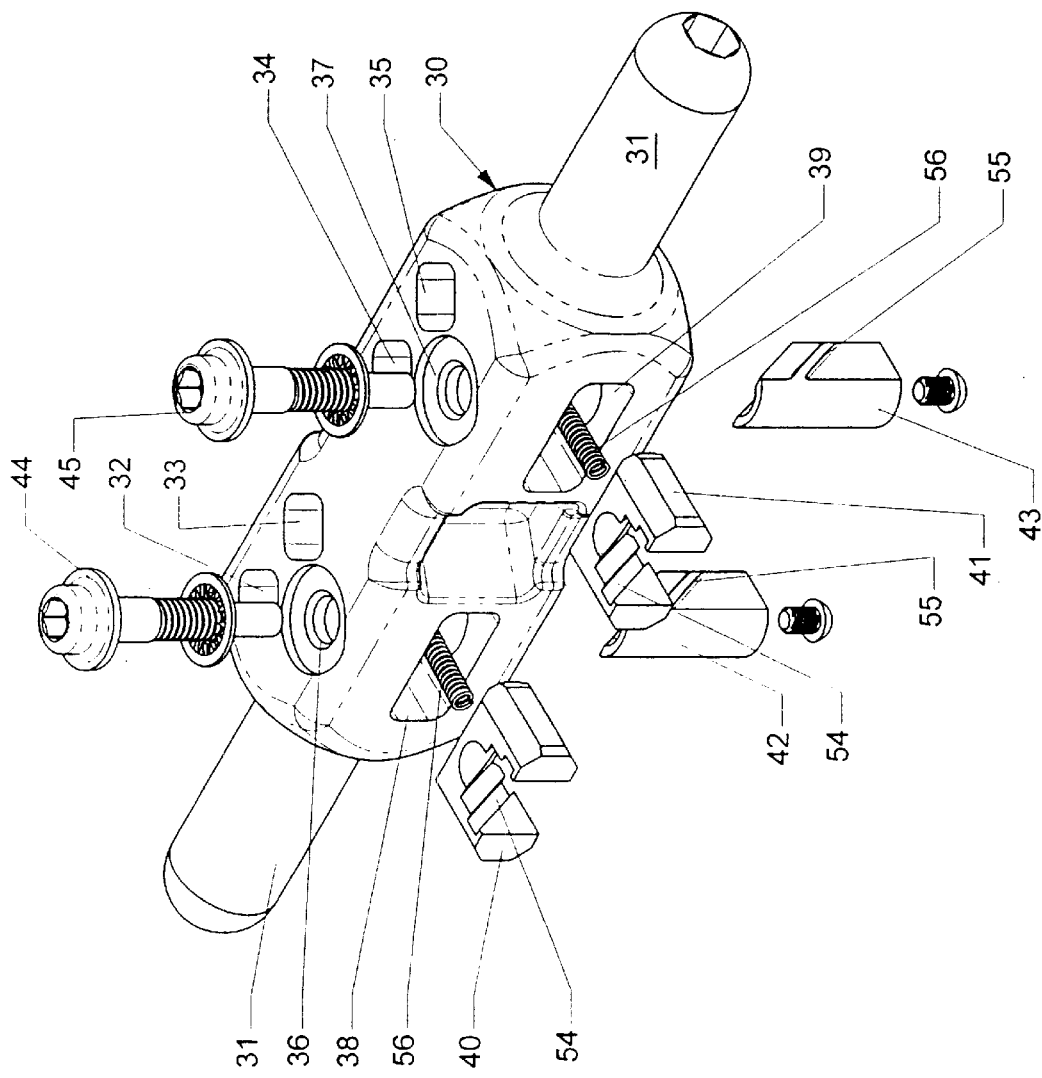
FIG. 3 is a partially exploded perspective view of an alternate embodiment of a pin clamping/mounting member employed in the frame system of the present invention.
Figure 4:
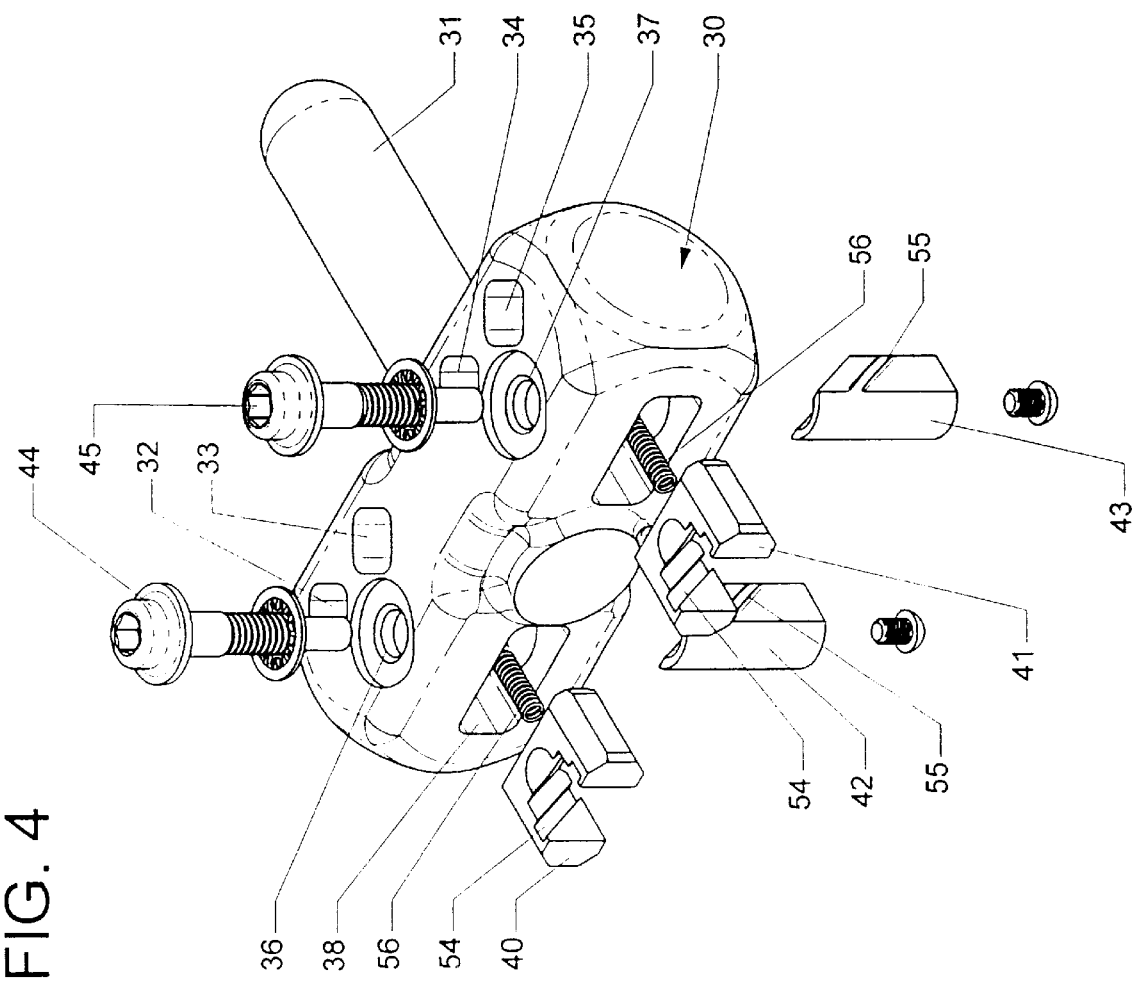
FIG. 4 is a partially exploded perspective view of a further alternate embodiment of a pin clamping/mounting member of the present invention.

As shown in FIGS. 2, 3, and 4, each of the alternate configurations of pin clamping/mounting member 30 preferably incorporates pin receiving cavities which comprise a substantially rectangular or square-shaped cross-section. Although any desired shape may be employed, this square or rectangular shape is preferred in order to enable a wide variety of anchor pins to be easily receiving therein. In this way, anchor pins having varying diameters or shapes are able to be inserted into the pin receiving cavities and secured therein by abutting, sandwiching engagement between the wall of the cavity and the leading edge or surface of the center portion 50 of clamping plates 40 and 41.

In addition, as depicted in these Figures, each pin clamping/mounting member 30 comprises four separate pin receiving cavities 32, 33, 34, and 35. Although any desired number of cavities may be employed, four cavities are preferred for providing substantial universality.

In most procedures involving larger bones, two or four anchor pins are mounted in the bone part for use in stabilization. As a result, regardless of which number of pins are used, pin mounting/clamping member 30 of this invention may be employed. By employing the construction detailed above, each clamping plate 40 and 41 is brought into abutting, locking engagement with the anchor pins, regardless of whether one or two pins are present. As a result, universal, secure, affixation of pin clamping/mounting member 30 to the desired bone part is attained.

As discussed above in reference to FIG. 1, pin clamping/mounting member 30 affixed to upper part 22 of bone 21 incorporates two connecting rods 31 extending from opposite terminating ends thereof. Each of these connecting rods 31 are employed for securely affixing member 30 and upper part 22 of bone 21 to the remainder of the external fixation frame assembly 20 of this invention.

As depicted in FIG. 1, broken parts 22 and 23 of leg bone 21 are secured and maintained in the desired position for healing by securely interconnecting the two pin clamping/mounting members 30 to each other by clamps 60 and stabilizing rods 61. As detailed below, once this frame assembly is completed, upper part 21 and lower part 22 are securely mounted to each other in abutting, contacting, slip-free engagement in order to enable complete healing to be achieved.

In order to form frame assembly 20, a clamp assembly 60 is affixed to each connecting rod 31 of each pin clamping/mounting member 30, while also securely affixing a portion of a stabilizing rod 61 in each clamp assembly 60. In achieving this result, in accordance with the present invention, clamp assembly 60 is preferably constructed in the manner depicted in FIGS. 9, 10, and 11.

As shown therein, clamp assembly 60 preferably comprises two separate and independent clamp members 64, each of which comprise a generally C-shape clamping zone 69, with movement control plates 66 and 67 extending from each terminating end of C-shaped clamping zone 69. In order to assure that clamp assembly 60 is able to be employed for interconnecting two stabilizing rods 61 or connecting rods 31 in any desired angular position relative to each other, each clamp member 64 is arcuately pivotally movable relative to the other into any desired angular relationship. This construction and operation is further detailed below.

In the preferred construction, clamp member 64 incorporates a co-axially aligned screw receiving cavity 68 extending through each plate. In addition, each movement control plate 67 of each clamp member 64 comprises a circular shaped tooth array formed in the outer surface thereof, with the pattern of the tooth array being constructed for mating interengagement with each other. As depicted, each clamp assembly 60 comprises two clamp members 64, with the tooth array of each movement control plate 67 of each clamp member 64 being mounted in cooperating interengagement with each other.

In order to maintain clamp members 64 in the desired assembled position, as well as control the secure clamping engagement of clamping zone 69 with the rod member mounted therein, clamp assembly 60 incorporates a clamping control screw 70 which extends through each of the receiving cavities 68 formed in each control plate 66 and 67 of each clamp member 64.

In the preferred embodiment, screw receiving cavity 68 of each movement control plate 66 comprises screw threads formed therein for threaded engagement with threaded zone 71 of screw 70. In addition, in the preferred construction, clamping control screw 70 comprises threaded zone 71 formed at its distal end, with head portion 72 formed at its proximal end. Radially extending flange 73 is also formed on screw 70, directly adjacent head portion 72. Finally, shank portion 74 extends from flange 73 to threaded zone 71 and preferably comprises a generally smooth outer surface having a diameter for passing through cavity 68 of control plates 66 and 67.

In the preferred assembled construction, a washer 75 is mounted about screw 70 between flange 73 and the outer surface of control plate 66 for assuring that complete controlled movement of control plates 66 and 67 is attained. Finally, an enlarged handle 76 is mounted about head portion 72 in contact with flange 73 for providing controlled rotational movement of screw 70 to achieve small or incremental clamping adjustments.

When fully assembled, clamp member 64 are mounted to each other in a substantially vertically stacked position with the circular tooth array of each movement control plate 67 interengaged with the other. In addition, this position is maintained by telescopically inserting clamping control screw 70 through the screw receiving cavity 68 of each of the control plates 66 and 67 of each clamp member 64 until flange 73 and head 72 of screw 70 is engaged with the outside surface of control plate 66 of the upper clamp member 64, while threaded zone 71 of screw 70 is threadedly engaged with the screw threads formed in receiving cavity 68 of control plate 66 of the lower clamp member 64.

Once fully assembled, the arcuate rotation of clamping control screw 70 in a first direction causes screw 70 to be telescopically advanced through cavities 68. However, once flange 73 contacts washer 75 and/or the outer surface of control plate 66 of upper clamp member 64, any further rotation of screw 70 causes movement control plates 66 and 67 of each clamp member 64 to be advanced towards each other by compressing against the spring force provided by C-shaped clamping zone 69. Furthermore, this movement causes the clamping diameter of C-shaped zone 69 to be reduced, effectively securing a rod member inserted therein.

As is evident from the foregoing detailed discussion, only control plate 66 of the lower clamping member 64 is threadedly engaged with screw 70, since the remainder of shank portion 74 is smooth. As a result, the rotational movement of screw 70 effectively controls the tightening of clamp members 64 as well as the loosening of clamp member 64, when desired, by rotating screw 70 in the opposite direction.

By employing this construction, clamp members 64 of clamp assembly 60 are able to be arcuately pivoted relative to each other about the axis defined by control screw 70. As a result, any desired connecting rods 31 and/or stabilizing rods 61 are securely affixed to each other in any required angular relationship. In this way, frame assembly 20 is quickly and easily created in the precisely desired configuration and orientation.

In order to enhance the arcuate movement and precision placement of clamping 64 relative to each other, clamp assembly 60 of the present invention incorporates bushing 80 which is mounted in and extends between screw receiving cavities 68 of each control plate 67 of both upper and lower clamp members 64. By incorporating bushing 80 and constructing bushing 80 to extend between both clamp members 64, the precise vertical alignment of the clamp members is maintained, regardless of the clamp forces being imposed thereon.

In most prior art clamp assemblies, tilting or pivoting of one clamp member relative to the other often occurs when the clamping forces are imposed. As a result, precise arcuate positioning of the clamping members relative to each other is not attainable. However, by incorporating bushing 80, this prior art inability is overcome and any desired precision arcuate alignment and positioning is achieved.

An additional benefit provided by this construction of the present invention is the ability to incorporate a circular tooth array on the face of each control plate 67 which provides extremely fine teeth and grooves, unattainable with prior art systems. In this way, cooperating clamp members 64 are able to be fine tuned into precise arcuate relative positions, thereby assuring the creation of frame assembly 20 which is optimized in every respect.

Another important feature provided by clamp assembly 60 of the present invention is the incorporation of friction means in clamping zone 69 of each clamp jaw 65 of each clamp member 64. By providing this unique feature, any connecting rod 31 or stabilizing rod 61 positioned in clamping zone 69 is retained in the set position, until moved by the surgeon. As a result, assembly and adjustments of the external fixation frame assembly 20 are able to be made easily and conveniently, without any slippage or movement of the rods in the clamps.

Figure 9:
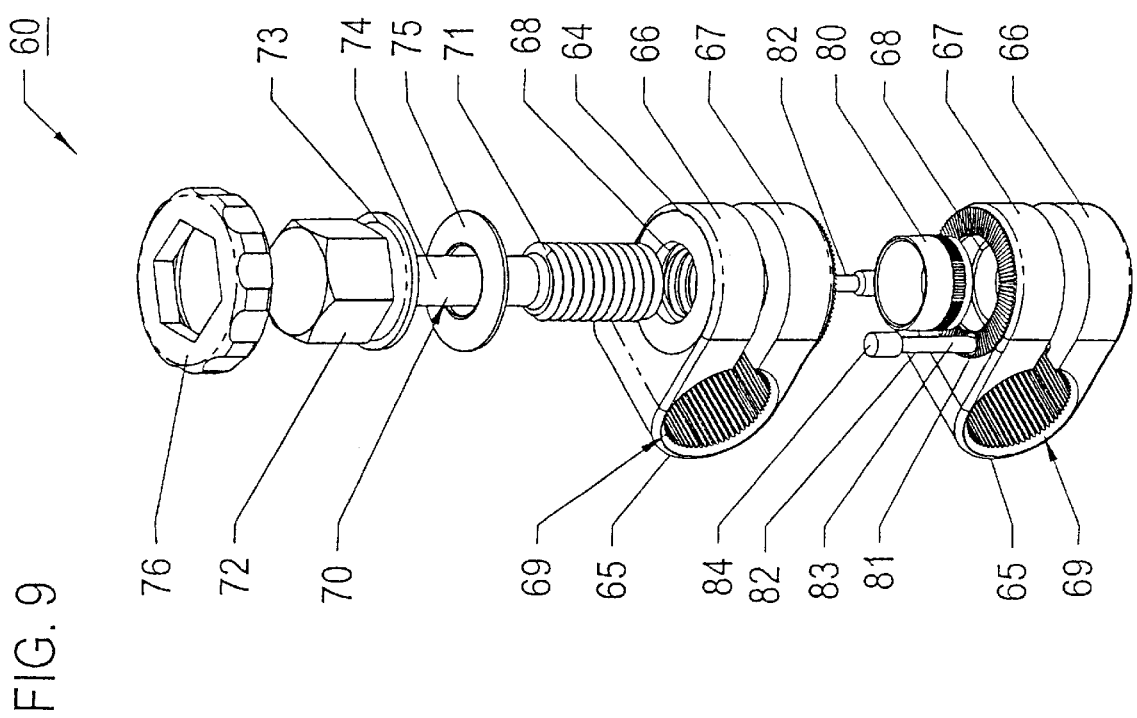
FIG. 9 is an exploded perspective view of one embodiment of a clamp assembly employed in the frame system of the present invention.
Figure 11:
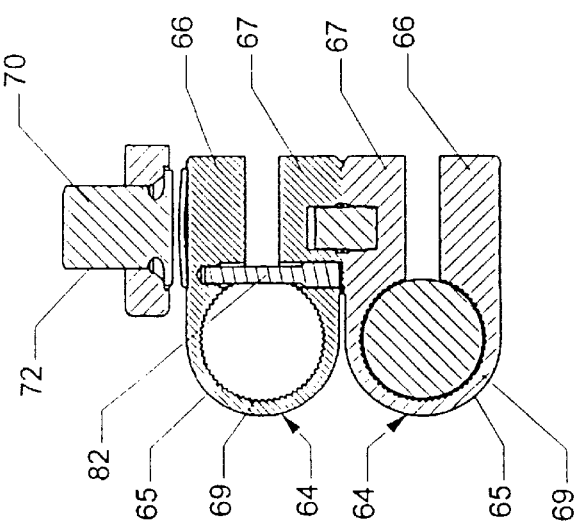
FIG. 11 is a cross-sectional side elevation view of the clamp assembly of FIG. 10.
Figure 10:
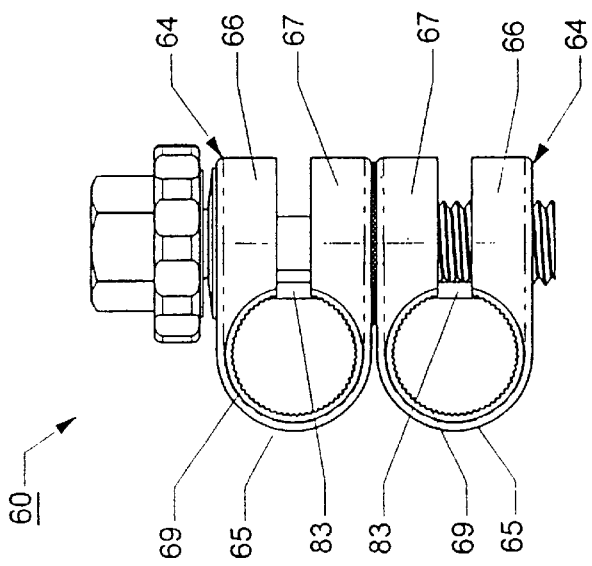
FIG. 10 is a side elevation view of the clamp assembly of FIG. 9 shown fully assembled.

Although alternate constructions may be employed without departing from the scope of this invention, the preferred constructions for providing friction means in clamp assembly 60 is depicted in FIGS. 9, 10, and 11. In this preferred embodiment, each clamping member 64 incorporates co-axially aligned pin receiving cavity 81 extending through control plates 67 and 66. Preferably pin receiving cavity 81 is positioned in close proximity to C-shaped clamping jaws 65, with the axis thereof being parallel to the axis of screw receiving cavity 68.

This preferred embodiment is completed by providing an elongated friction pin 82 and telescopically inserting and securing friction pin 82 in elongated cavity 81. By properly mounting and positioning friction pin 82 in the manner detailed above, friction pin 82 extends between control plates 66 and 67, with intermediate portion 83 of the shaft of pin 82 extending into clamping zone 69. By employing this construction, any connecting rod 31 and/or stabilizing rod 61, which comprises a diameter for being secured in C-shaped clamping jaws 65, will contact intermediate portion 83 of friction pin 81 whenever mounted in C-shaped clamping jaw 65.

As a result, when connecting rod 31 and/or stabilizing rod 61 is inserted into C-shaped clamping jaw 65, intermediate portion 83 of friction pin 82 is flexed away from clamping zone 69, while being maintained in frictional engagement with the rod due to the inherent spring force of pin 82 attempting to return to its normal straight configuration. In this way, a constant frictional engagement force is maintained on any connecting/stabilizing rod inserted into C-shaped clamping jaw 65, forcing the rod into contact with the surface of jaw 65.

This biasing force must be overcome when telescopically inserting and advancing any connection rod 31 and/or stabilizing rod 61 in C-shaped clamping jaw 65. However, whenever a desired relative position is attained, no clamping adjustment needs to be made. Instead, the biasing force and frictional engagement of pin 82 with the rod member and the walls of jaw 65 is sufficient to maintain the rod member in the set position.

By employing this construction, any desired construction for frame assembly 20 is quickly and easily achieved and fully completed in an initial orientation, with complete assurance that slippage or sliding of the components will not occur, even though secure tightening of each clamp member 64 has not been attained. In this way, the present invention allows the surgeon to fine tune or adjust frame assembly 20 in order to achieve a precision construction. However, throughout the entire adjustment process, secure clamping is avoided since friction pin 82 of each clamp member 64 provides the desired securement of any rod member in any position during the adjustment process.

Once all of the components of frame assembly 20 have been placed in their precisely desired position and orientation, each rod member is securely clamped in jaw 65 of each clamping member 64. Since secure clamping forces are only required when the final configuration of frame assembly 20 has been completed, the construction and adjustment of frame assembly 20 is achieved with substantially enhanced ease, simplicity, and convenience.

As best seen in FIGS. 9 and 11, friction pin 82 comprises an enlarged head 84 which has a diameter greater than intermediate portion 83. In addition, pin receiving cavity 81 is constructed to receiving and retain enlarged head 83 of pin 82.

In the preferred embodiment, the head receiving portion of cavity 81 is formed in control plate 67 of each clamp member 64. As shown, convenient location for cavity 81 with the head receiving portion thereof is along the tooth and groove array of plate 67. This location and position is preferred since the tooth/groove array of each control plate 67 is maintained in abutting, contacting interengagement with the tooth/groove array of the adjacent control plate 67 of the adjacent clamp member 64.

As a result, positive securement of friction pin 82 in cavity 81 is provided and any possibility of dislodgement or movement of pin 82 is prevented. In this way, assurance is provided that friction pin 82 is always present in clamping zone 69 in order to provide the desired slip-free, fully retained assembly benefits of the present invention.

Figure 13:
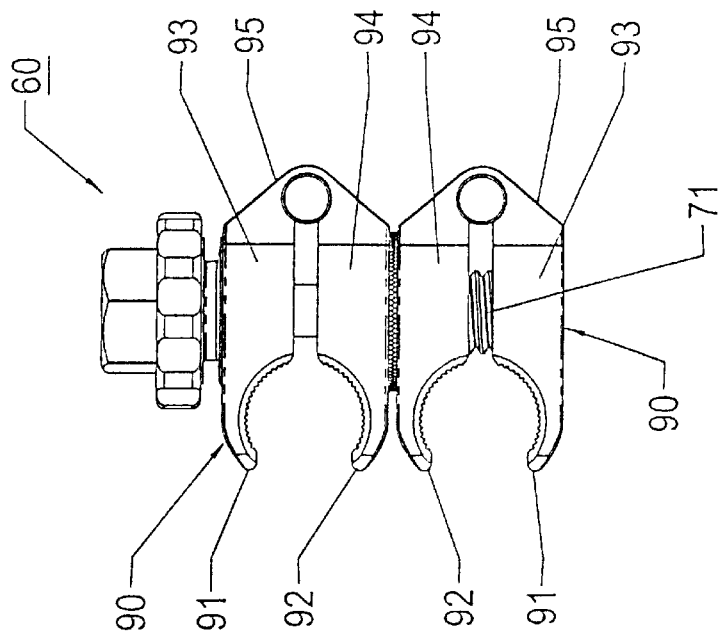
FIG. 13 is a side elevation view of the clamp assembly of FIG. 12 shown fully assembled.
Figure 12:
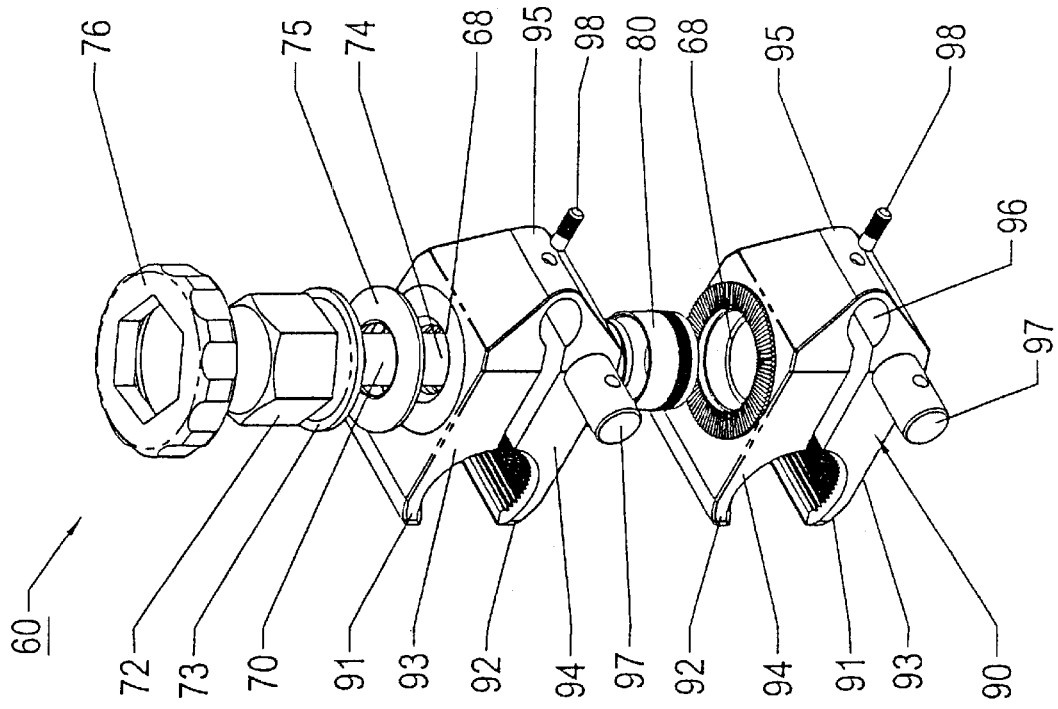
FIG. 12 is an exploded perspective view of another embodiment of a clamp assembly of the present invention.

In FIGS. 12 and 13, an alternate embodiment of clamp assembly 60 is depicted. In this embodiment, two separate and independent clamp members 90 are mounted in a vertically stacked array, as detailed above. However, in this embodiment, each clamp member 90 comprises separate and independent clamping jaws 91 and 92. In certain applications, telescopic entry into the clamping jaw is not possible, as is required in C-shaped clamping jaw 65. Consequently, two separate and independent clamping jaws 91 and 92, as depicted in FIGS. 12 and 13, are employed which enable any desired connecting rod 31 and/or stabilizing rod 61 to be inserted into jaws 91 and 92 with ease and simplicity.

In this embodiment, each clamp member 90 comprises a movement control plate 93 which is interconnected with jaw 91 and a movement control plate 94 which is interconnected with jaw 92. Movement control plates 93 and 94 are positioned in juxtaposed, spaced, vertically aligned, cooperating relationship with each other, enabling clamping jaws 91 and 92 to operate in the desired manner.

In order to provide clamping jaws 91 and 92 with the desired, integrated spring biasing force, clamp member 90 also comprises an interconnecting wall member 95 which extends between movement control plates 93 and 94 on the side thereof opposite clamping jaws 91 and 92. In this way, an integrated spring force is provided to clamping jaws 91 and 92 which tends to open jaws 91 and 92, unless counteracted by a closing or clamping force.

The remainder of the construction of clamp member 90 is substantially equivalent to the construction of clamp assembly 60 as detailed above. In this regard, screw or boss receiving cavities 68 are formed in movement control plates 93 and 94, with threaded zones being formed in cavities 68 of control plate 93, and a smooth boss receiving zone being formed in cavity 68 of control plate 94. In addition, as detailed above, the top surface of control plate 94 of each clamp member 90 comprises a circular array of teeth and grooves, for enabling the desired mating, interengagement and arcuate rotational movement of each clamp member 90 relative to the other clamp member 90.

In addition, bushing 80 is employed for mounted interengagement between mating control plates 94 by inserting bushing 80 in cavities 68 of each control plate 94. In this way, as detailed above, tilting or skewing of clamp members 90 relative to each other during the clamping process is prevented.

In addition, clamping control screw 70 is telescopically inserted through screw receiving cavities 68 of each movement control plate 93 and 94 with threaded zone 71 of control screw 70 being engaged in cavities 68 of the lowermost control plate 93. In addition, with clamping control screw 70 incorporating head 72, flange 73, shank portion 74 and washer 75, all as described above, any arcuate rotation of control screw 70 in a first direction causes jaws 91 and 92 of each clamping member to advance toward each other, securely engaging and lockingly retaining any rod member inserted therebetween. In addition, as detailed above, handle 76 may be mounted, if desired, to head 72 of screw 70 in order to enable precise, controlled, rotational movement of screw 70.

Although constructions of this general nature have been employed in the prior art, all of these prior art constructions suffer from the common deficiency that any interconnecting wall member 95 is capable of being crushed by excessive clamping forces imposed thereon. In such instances, the resulting clamp is incapable of being used.

In the present invention, a unique construction has been developed which prevents any unwanted crushing or crimping of interconnecting wall member 95. In accordance with the present invention, the interior surface of interconnecting wall member 95 is arcuately rounded, forming pin receiving zone 96. The construction of each clamp member 90 is completed by positioning pivot pin 97 in pin receiving zone 96 of wall member 95, and securely maintaining pivot pin 97 in the precisely desired position by mounting securing rod 98 through apertures formed in wall 95 and pin 97. In this way, pivot pin 97 is securely retained in contacting engagement with wall member 95, imparting thereto the desired resistance force for preventing crushing or bending of wall member 95, while enhancing the inherent spring force provided by wall member 95.

As is evident from the foregoing detailed discussion, by securely mounting pivot pin 97 in pin receiving zone 96 of wall member 95, wall member 95 is incapable of being crushed or bent by the application of compressive forces thereto. In addition, the inherent spring force provided by wall member 95 to jaws 91 and 92 is enhanced and increased. As a result, the construction provided by this embodiment of the present invention clearly establishes an open clamping jaw construction for clamp assembly 60 which completely eliminates all of the prior art difficulties and drawbacks, and provides a clamp assembly 60 which is capable of being used with complete assurance that failure of the clamp assembly during its use cannot occur.

Figure 14:
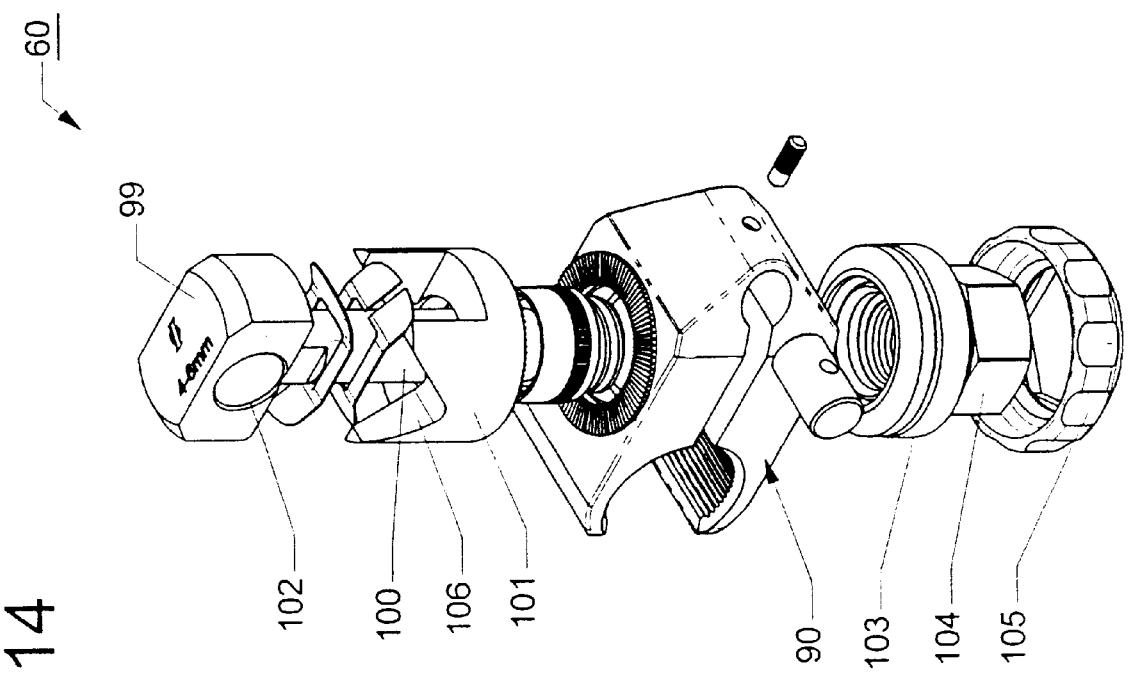
FIG. 14 is an exploded perspective view of a further alternate embodiment of a clamp assembly of the present invention.

In FIG. 14, a further alternate embodiment of clamp assembly 60 is shown. In this embodiment, clamping member 90 is employed and constructed in the manner detailed above. However, in constructing this embodiment of clamp assembly 60, only one clamp member 90 is used, with rod receiving head 99 being formed at one end of elongated shaft 100, which is threadedly engaged in control plate 93 of clamp member 90. In addition, a cooperating rod receiving and securing member 101 is mounted about shaft 100 in cooperative association with head 99.

Using this construction, any desired rod having the proper diameter is inserted through aperture 102 formed in head 99 and secured therein by V-shaped receiving zone 1002 formed in receiving/securing member 101. The secure, threadedly, affixed interengagement of these components are provided by employing collar 103, which comprises a head 104 and handle 105 and is constructed for threaded interengagement with the terminating end of shaft 100. As result, by rotationally moving handle 105 or head 104, the secure clamping affixation of this embodiment of clamp assembly 60 is achieved.

Using this construction, any desired rod having the proper diameter is inserted through aperture 102 formed in head 99 and secured therein by V-shaped receiving zone 106 formed in receiving/securing member 101. The secure, threadedly, affixed interengagement of these components are provided by employing collar 103, which comprises a head 104 and handle 105 and is constructed for threaded interengagement with the terminating end of shaft 100. As result, by rotationally moving handle 105 or head 104, the secure clamping affixation of this embodiment of clamp assembly 60 is achieved.

In this regard, broken or damaged fingers, jaws, wrists, and the like are examples of areas which require a substantially smaller, lighter, and more delicate external fixation frame system. By referring to FIGS. 15–22, along with the following detailed disclosure, the construction and operation of the preferred component for such an external fixation frame system of the present invention can best be understood.

Figure 15:
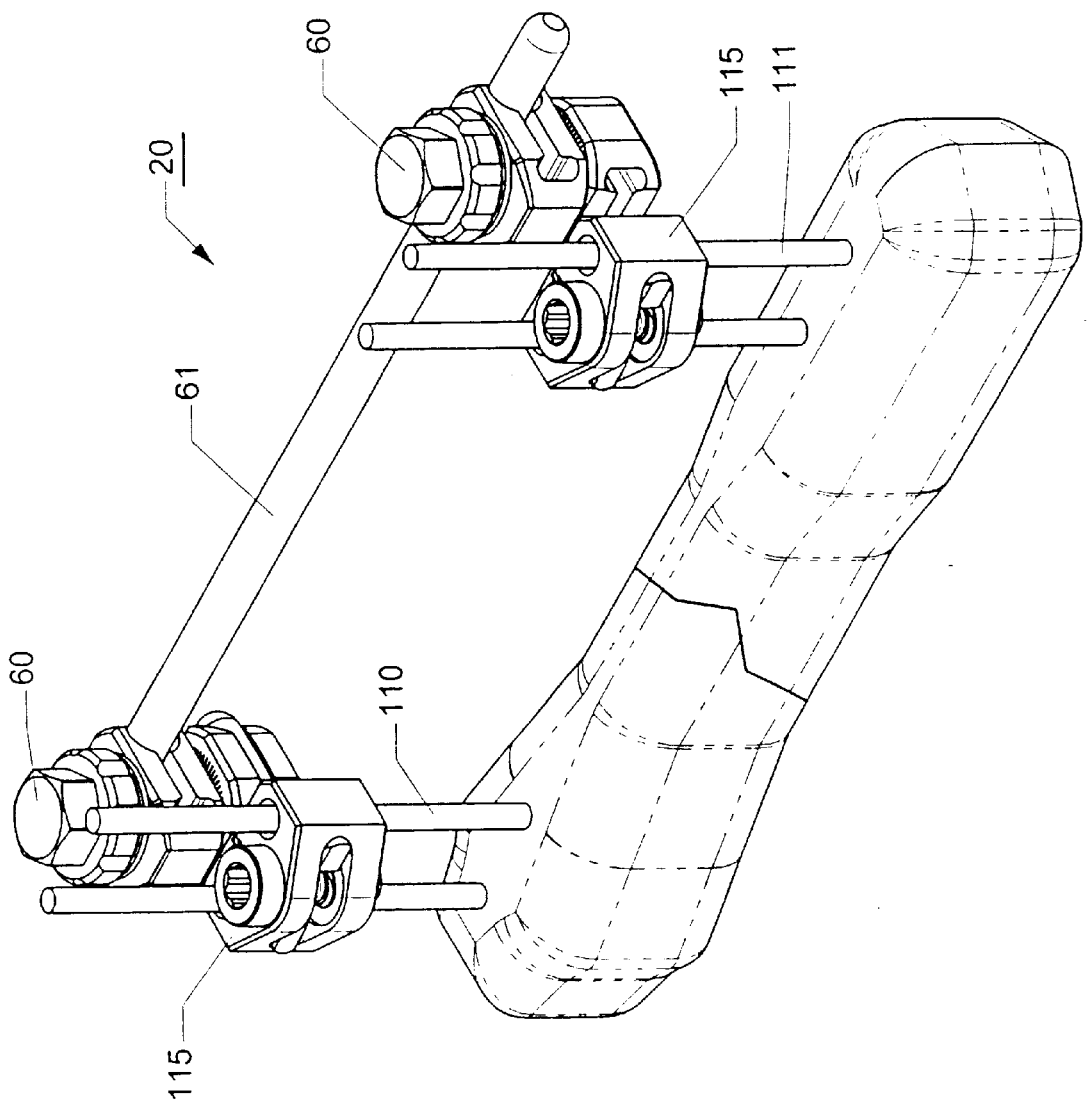
FIG. 15 is a perspective view depicting an alternate embodiment of a fully assembled external fixation bone stabilizing frame system of the present invention securely mounted for stabilizing a broken finger bone.

In FIG. 15, one typical application for employing the smaller components of the frame system of the present invention is depicted for holding and stabilizing small broken bones, such as are found in the hand, fingers and wrist. As depicted, one application of employing the external fixation, bone stabilizing frame system 20 of the present invention is setting a broken or fractured finger bone.

In this regard, the first step in stabilizing a broken or fractured finger is the mounting of at least one anchor pin 110 on one side of the break or fracture, and mounting at least one additional anchor pin 111 on the opposite side of the brake or fracture. In each instance, the anchor pins are securely affixed directly into the bone of the finger, extending outwardly therefrom. As is well-known in the industry, in any situation where soft tissue or opened wounds are present, along with a broken or fractured bone, surrounding of the broken bone with a cast or splint is not possible. Consequently, external fixation frame assemblies are required.

Using the outwardly extending anchor pins 110 and 111, frame system 20 of the present invention is created in order to form the required bone stabilizing frame system for maintaining the broken finger bones in the precisely desired, aligned and engaged position to promote complete healing. In forming the desired frame system 20, two separate and independent pin clamping/mounting members 115 are employed. As depicted, each pin clamping/mounting member 115 is affixed to one of the anchor pins and then interconnected with each other by clamp assemblies 60 and stabilizing rod 61.

In order to best understand the construction and operation of pin clamping/mounting member 115, reference should be made to the following detailed description along with FIGS. 16–22. By referring to these Figures and the following detailed disclosure, the unique construction and operational details of pin clamping/mounting member 115 of the present invention can best be understood.

Figure 17:
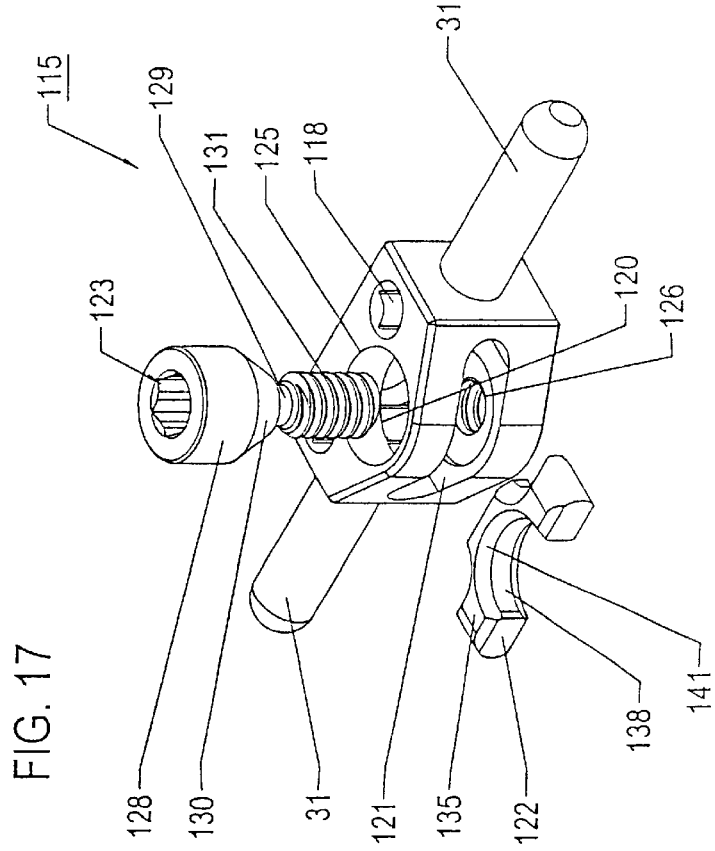
FIG. 17 is an exploded perspective view of an alternate embodiment of a pin clamping/mounting member of the present invention.
Figure 16:
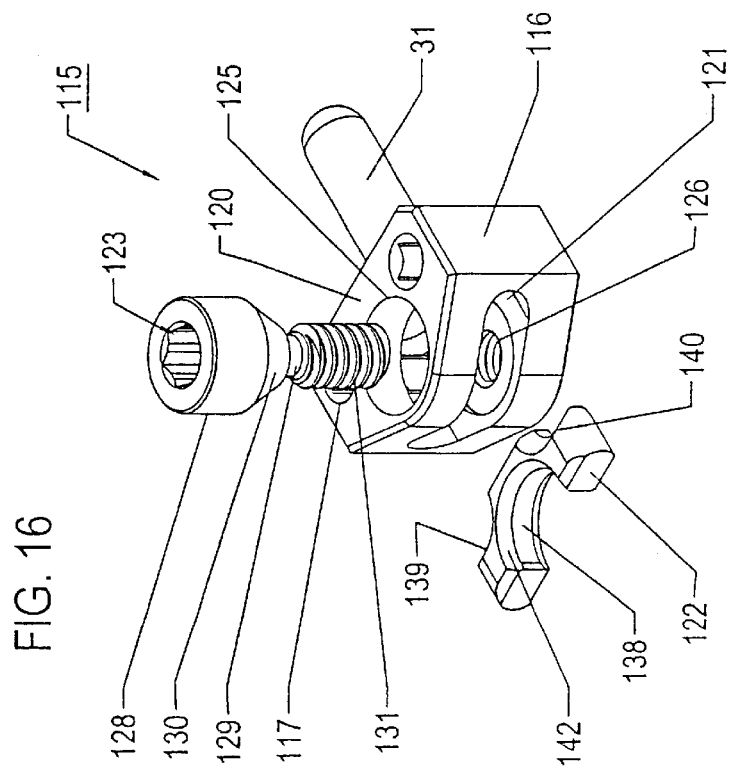
FIG. 16 is an exploded perspective view of one embodiment of a pin clamping/mounting member employed in the frame system of FIG. 15.
Figure 18:
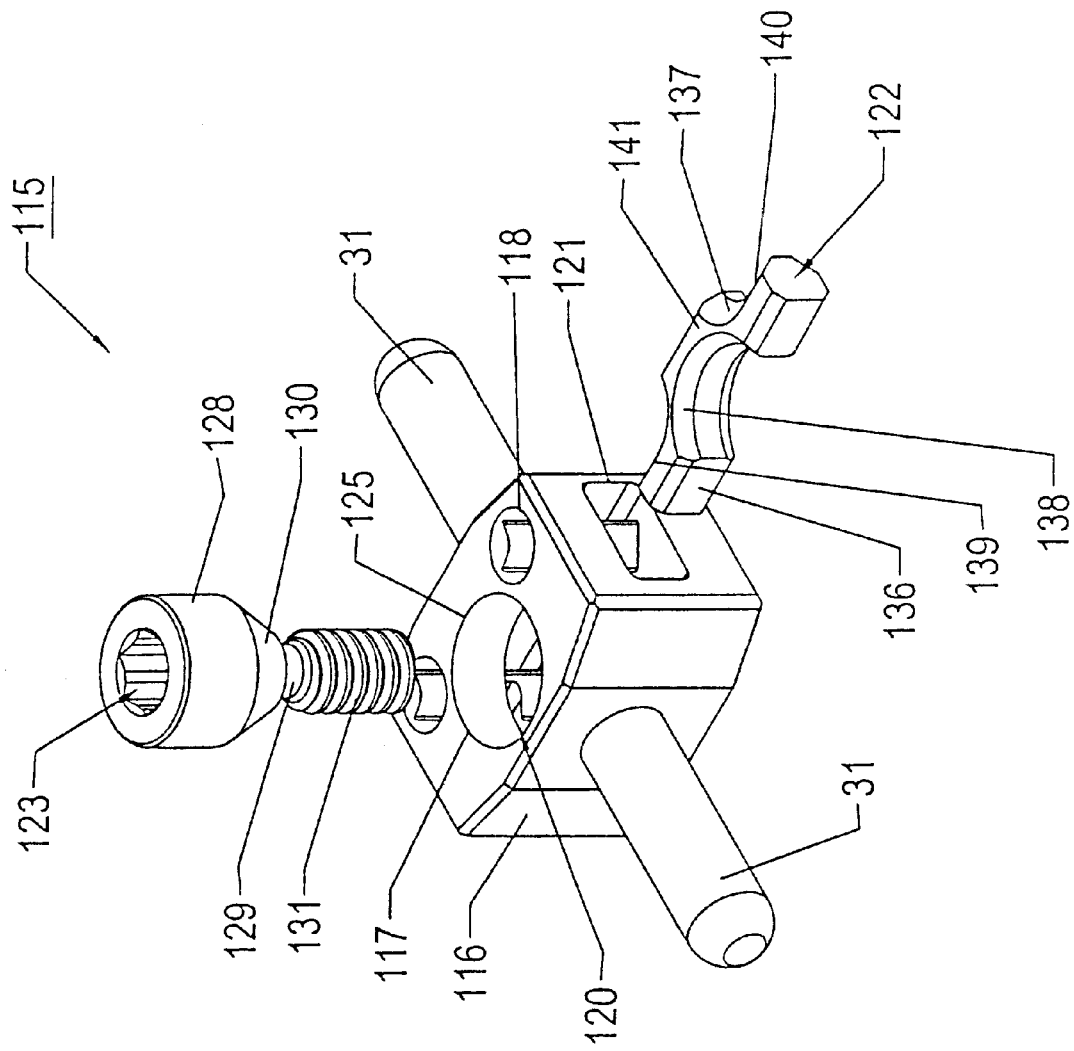
FIG. 18 is an exploded perspective view of a further alternate embodiment of the pin clamping/mounting member of the present invention.
Figure 19:
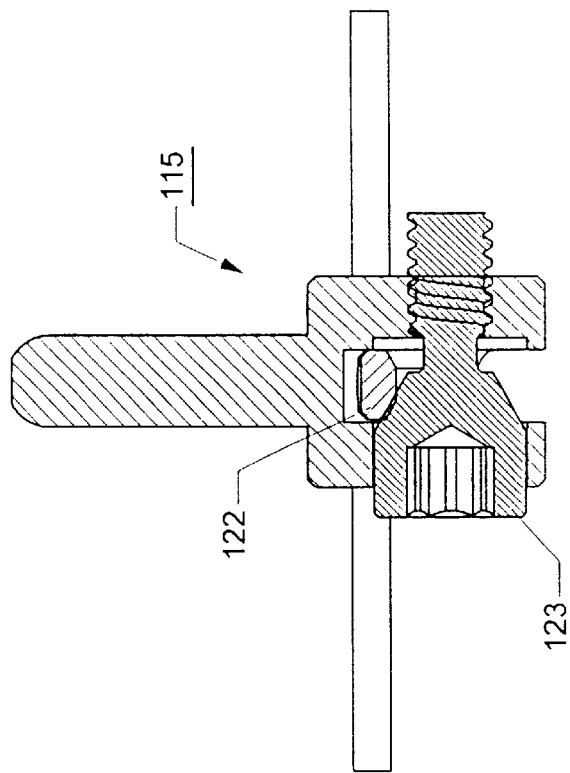
FIG. 19 is a top plan view of the pin clamping/mounting member of FIG. 16.
Figure 20:
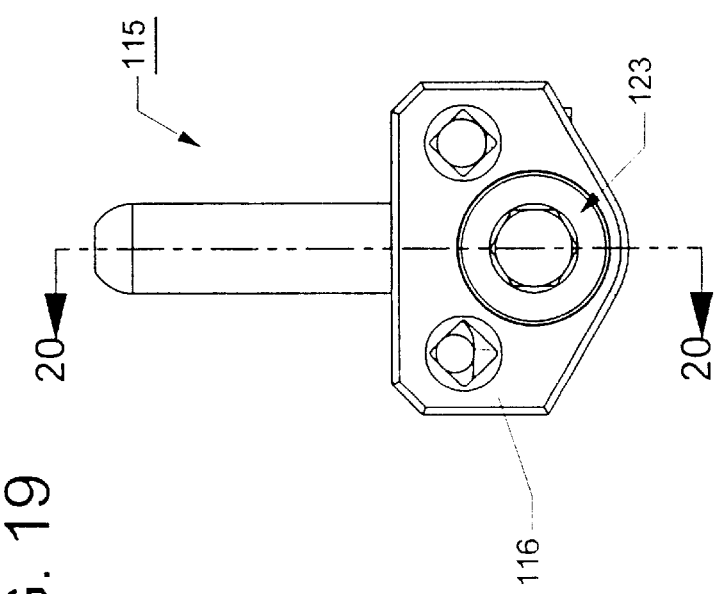
FIG. 20 is a cross-sectional side elevation view of the pin clamping/mounting member of the present invention taken along line 20—20 of FIG. 19.
Figure 22:
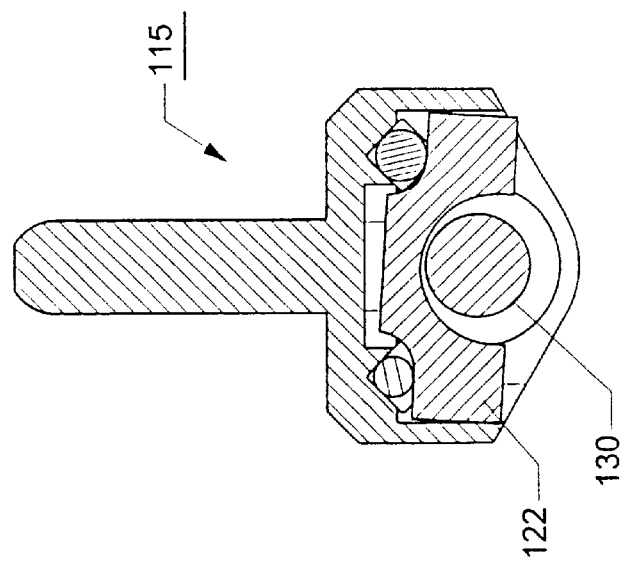
FIG. 22 is a cross-sectional plan view of the pin clamping/mounting member of the present invention taken along line 22—22 of FIG. 21.
Figure 21:
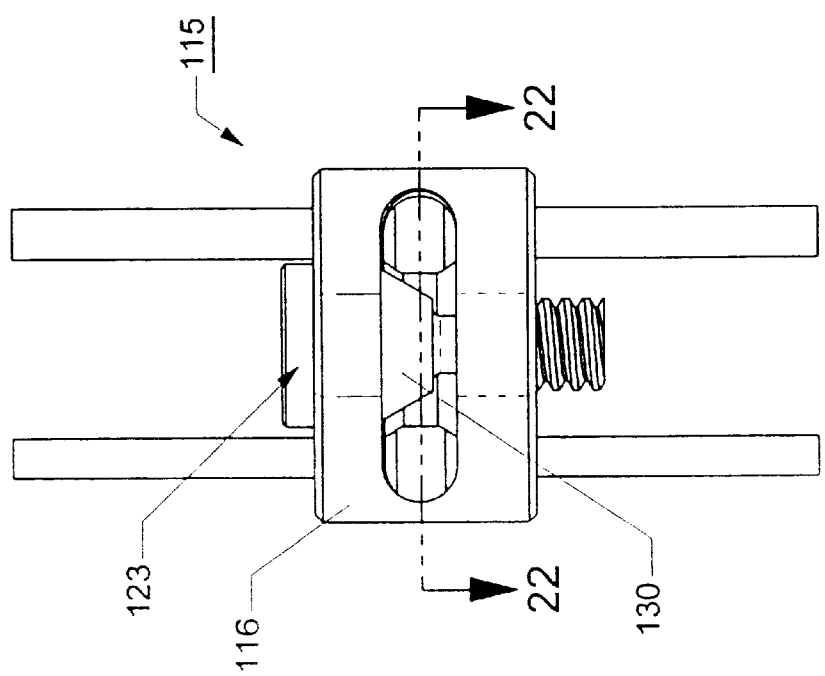
FIG. 21 is a rear view of the pin clamping/mounting member of the present invention.

As shown in FIGS. 16, 17, and 18, pin clamping/mounting member 115 may incorporate one or two connecting rods 31, with one or two connecting rods 31 being mounted at opposite ends or substantially mid-way along the length of mounting member 115. Regardless of the position or number of connecting rods 31 mounted to pin clamping/mounting member 115, the overall construction of clamping/mounting member 115 is substantially identical. In order to best understand this construction, reference should be made to FIGS. 16, 17, and 18, wherein these alternate embodiments are depicted and fully detailed below.

In the preferred construction, pin clamping/mounting member 115 incorporates housing 116 in which are formed two separate and independent pin receiving cavities or apertures 117 and 118, extending from the top surface of housing 116 through to the bottom surface thereof. In addition, as is more fully detailed below, each pin receiving cavity 117 and 118 preferably comprise a generally rectangular or square cross-sectional shape.

Furthermore, a clamping screw receiving cavity 120 is formed adjacent pin-receiving cavities 117 and 118 also extending from the top to the bottom surface of housing 116. In the preferred construction, clamping screw receiving cavity 120 comprises an upper enlarged screw receiving zone 125 and a lower zone 126 which comprises a screw thread configuration. In addition, the axis of each pin-receiving cavity 117 and 118 as well as the axis of screw receiving cavity 120 are all formed substantially parallel to each other.

Finally, the construction of housing 116 is completed by forming an enlarged interior slot 121 in one side wall of housing 116, with slot 121 dimensioned for receiving and retaining clamping wedge 122. As clearly shown in FIGS. 16 and 17, slot 121 extends through screw receiving cavity 120, effectively forming upper zone 125 and lower zone 126.

In the preferred embodiment, clamping wedge 122 comprises a generally rectangular-shaped bar 135 incorporating generally parallel sides 136 and 137. Side 136 incorporates an arcuately curved zone 138 which is centrally disposed thereon and incorporates a sloping or beveled surface 142. In addition, side 137 incorporates two arcuately curved zones 139 and 140 formed at opposite ends of side 137, with a substantially straight, flat, intermediate zone 141 extending therebetween and positioned forward of curved zones 139 and 140. As detailed below, by employing this construction, secure abutting, contacting engagement of anchor pins of any desired diameter, or even different diameters, are capable of being securely engaged and clampingly retained by member 115.

The overall construction of pin clamping/mounting member 115 is completed by providing wedge clamping screw 123, which is constructed for telescopic insertion and secure retention within cavity 120. In the preferred construction, wedge clamping screw 123 comprises substantially circular-shaped head 128 with shaft 129 extending therefrom. In addition, beveled or sloping section 130 extends between head 128 and shaft 129, with the construction of wedge clamping screw 123 being completed by forming threaded portion 131 along the distal end of shaft 129. By employing this construction, once wedge clamping screw 123 is telescopically inserted into screw receiving cavity 120, threaded portion 131 matingly engages with threaded zone 126, while head 128 of screw 123 is able to pass through upper zone 125.

In FIGS. 19–22, the embodiment of pin clamping/mounting member 115 of FIG. 16 is depicted in detail, showing member 115 in use, securely clamping and engaging two anchor pins having different diameters. As is evident from a review of these Figures, pin clamping/mounting member 115 is capable of secure, clamping interengagement with small, thin or narrow anchor pins, as commonly employed with smaller and more delicate bone members. In addition, regardless of the diameter of the small anchor pins that are employed for securing the more delicate bone fragments, pin clamping/mounting member 115 is capable of secure clamping interengagement therewith, even in those instances where anchor pins of different diameters are required to be secured by a single pin clamping/mounting member 115.

When employing the present invention, once anchor pins 110 and/or 111 are passed through pin-receiving apertures 117 and 118, member 115 is quickly and easily securely clamped therewith by arcuately rotating wedge clamping screw 123. Once threaded portion 131 of wedge clamping screw 123 is threadedly engaged in lower zone 126, rotational movement of screw 123 in a first direction advances screw 123 downwardly, causing head portion 128 to enter receiving zone 125 of cavity 120.

As screw 123 continues to be moved in this downward direction, sloping or beveled section 130 of screw 123 is brought into controlled, contacting engagement with beveled surface 142 of arcuately curved section 138 of clamping wedge 122. As a result of this contact, controlled movement of clamping wedge 122 is provided by screw 123, causing wedge 122 to advance in slot 121 towards anchor pins 110 and 111 mounted in receiving cavities 117 and 118.

As the rotation of screw 123 continues, movement of clamping wedge 122 also continues until curved zones 139 and 140 are brought into abutting, contacting engagement with the anchor pins mounted in receiving cavities 117 and 118. Once secure, abutting, contacting, clamping interengagement between wedge 122 and anchor pins 110 and 111 is attained, the rotation of screw 123 is halted.

In addition to providing the controlled advance of clamping wedge 122 into secure, abutting, clamping engagement with anchor pins 110 and 111 mounted in receiving cavities 117 and 118, the construction of clamping wedge 122 also allows arcuate pivoting movement of clamping wedge 122 relative to slot 121. As a result, anchor pins having different diameters are capable of being securely clamped in a single member 115, with complete assurance that both anchor pins are securely, clampingly interengaged therewith.

In addition, this construction of pin clamping/mounting member 115 also enables engagement with single anchor pins mounted in either receiving cavity 117 or 118. In this way, regardless of the diameter of the anchor pins that are present, or the absence of one anchor pin, secure, locked, clamped engagement of the anchor pins as desired by the surgeon is capable of being achieved quickly and easily.

A further feature provided by the present invention is the ability to securely affix any desired anchor pins in either one or both pin receiving cavities 117 and 118, in a manner which provides secure, clamped interengagement of the anchor pin on three separate and independent sides thereof. As detailed above, pin receiving cavities 117 and 118 are preferably formed in a generally rectangular or square-shaped configuration.

As a result, any anchor pin positioned in pin receiving cavities 117 and/or 118 is forced to enter a corner of the rectangular or square-shaped clamping surface thereof as wedge 122 contacts a portion of the anchor pin. Once fully secured therein, the anchor pin contacts clamping wedge 122 on one portion or surface thereof, as well as two walls of pin receiving cavity 117 and 118 on two additional portions or surfaces thereof. As a result, positive secure, clamped engagement of any desired anchor pin in cavities 117 and 118 is obtained on three separate portions or sides by employing pin clamping/mounting member 115 of the present invention.

As shown in FIG. 15, the broken parts of the finger bone are secured and maintained in the desired position for healing by securely interconnecting two pin clamping/mounting members 115 to each other using clamps 60 and stabilizing rod 61. Once this frame assembly is completed, the two components of the finger bone are securely mounted to each other in abutting, contacting, slip-free engagement in order to enable complete healing to be achieved.

In forming frame assembly 20, clamp assemblies 60 are affixed to each connecting rod 31 of each pin clamping/mounting member 115, while also securely affixing a portion of stabilizing rod 61 to each clamp assembly 60. In achieving this result, in accordance with the present invention, clamp assemblies 60 are preferably constructed in the manner depicted in FIGS. 23 and 24.

Figure 23:
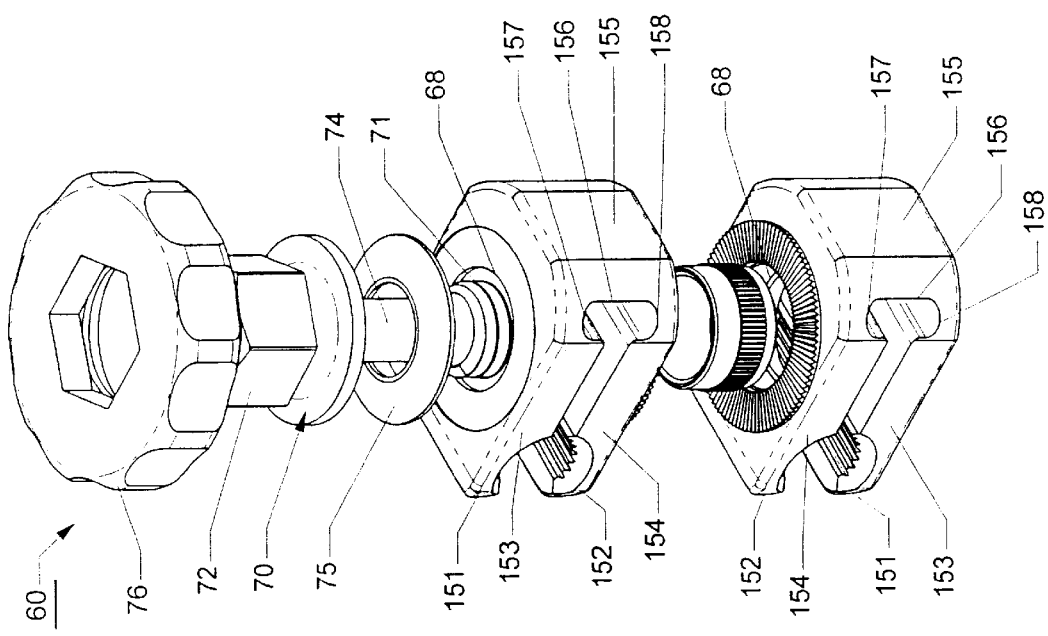
FIG. 23 is an exploded perspective view of a still further alternate embodiment of a clamp assembly of the present invention employed in the frame system of this invention.
Figure 24:
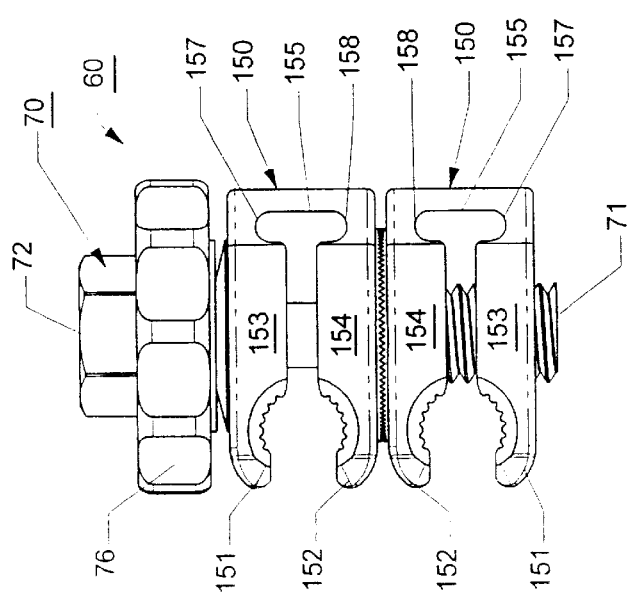
FIG. 24 is a side elevation view of the clamp assembly of FIG. 23 depicted fully assembled.

Although the clamp assembly constructions detailed above could be employed in this embodiment of the present invention, due to the extremely small size requirements imposed upon these components, the construction of clamp assembly 60 in the manner detailed above for the frame assemblies employed with the larger bones has been found to be difficult to achieve economically. Consequently, any alternate construction is preferred and the preferred construction for clamp assemblies 60 employed in constructing frame assembly 20 of the present invention for use with the smaller bone elements is depicted in FIGS. 23 and 24, and fully detailed below.

In this embodiment, clamp assembly 60 preferably comprises two separate and independent clamp members 150 mounted in a vertically stacked array, as detailed above in the alternate embodiments of clamp assemblies 60. In this embodiment, each clamp member 150 comprises separate and independent clamping jaws 151 and 152 for providing easy entry therein.

Furthermore, each clamp member 150 comprises a movement control plate 153 which is interconnected with jaw 151 and a movement control plate 154 which is interconnected with jaw 152. Movement control plates 153 and 154 are positioned in juxtaposed, spaced, vertically aligned, cooperating relationship with each other, enabling clamping jaws 151 and 152 to operate in the desired manner.

In order to provide clamping jaws 151 and 152 with the desired, integrated, spring biasing force, each clamp member 150 also comprises an interconnecting wall member 155 which extends between movement control plates 153 and 154 on the side thereof opposite clamping jaws 151 and 152. In this way, an integrated spring force is provided to clamping jaws 151 and 152 which tend to open jaws 151 and 152, unless counteracted by a closing or clamping force.

The remainder of the construction of clamp member 150 is substantially equivalent to the construction of clamp assembly 60 detailed above. In this regard, screw receiving cavities 68 are formed in movement control plates 153 and 154, with threaded zones being formed in cavities 68 of each control plate 153, while a smooth receiving zone is formed in cavity 68 of each control plate 154. In addition, if desired, the top surface of each control plate 154 may comprise a circular array of teeth and grooves, for providing the desired mating, interengagement and arcuate rotational movement of each clamp member 150 relative to the other clamp member 150.

In addition, clamping control screw 70 is telescopically inserted through screw receiving cavities 68 of each movement control plate 153 and 154, with threaded zone 71 of screw 70 being engaged in cavity 68 of the lowermost control plate 153. In addition, with clamping control screw 70 incorporating head 72, shank portion 74, and washer 75, as described above, any arcuate rotation of control screw 70 in a first direction causes jaws 151 and 152 of each clamping member 150 to advance towards each other, securely engaging and lockingly retaining any rod member inserted therebetween. In addition, as detailed above, handle 76 may be mounted, if desired, to head 72 of screw 70 in order to enable precise, controlled, rotational movement of screw 70.

In this embodiment of the present invention, unwanted crushing or crimping of interconnected wall member 155 is prevented by forming interior wall 156 of wall member 155 with a longitudinally extending, enlarged, generally oval or rectangular cross-sectional shape formed along the juncture between wall member 155 and movement control plates 153 and 154. As clearly depicted in FIGS. 23 and 24, the juncture between wall member 155 and movement control plate 153 comprises a smoothly rounded, arcuately curved zone 157 extending the entire width of wall member 155 at the juncture between these two components. Similarly, an arcuately curved, smoothly rounded zone 158 is formed at the juncture between wall member 155 and movement control plate 154. As a result, the generally oval or rectangular shaped configuration is obtained between these elements along interior wall 156.

By employing this construction, a resisted force imparted to wall member 155, preventing crushing or bending of wall member 155, while enhancing the spring force provided thereby. As result, the desirable qualities for clamp member 150 are obtained and unwanted crushing or bending of wall member 155 is prevented.

It will thus be seen that the objects set forth above, among those made apparent from the preceding description, are efficiently attained and, since certain changes may be made in the above article without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention, what we claim as new and desire to secure by Letters Patent is:

1. An externally mounted, adjustable bone stabilizing frame assembly constructed for engaging and holding a plurality of bone-mounted pins in a precisely desired orientation, said frame assembly comprising:
   A. a plurality of pin clamping and mounting members comprising:
      A. a plurality of pin receiving cavities constructed for receiving and securely clamping the bone-mounted pins therein,
      B. a clamping plate movably mounted in the pins clamping and mounting member in cooperating relationship with the pin receiving cavity,
      C. a wedge member movably mounted in the pin clamping and mounting member and controllably engaged with the clamping plate for controlling the movement thereof into engagement with the bone-mounted pins mounted in the pin receiving cavities; and
      D. at least one rod mounted to the pin clamping and mounting member and extending therefrom;
   B. at least one stabilizing rod positioned in cooperating relationship with the pin clamping and mounting members, and
   C. clamp assemblies securely mounted to the rods of the pin clamping and mounting member and the stabilizing rod for forming the desired securely engaged, external bone stabilizing frame assembly.

2. The externally mounted, adjustable bone stabilizing frame assembly defined in claim 1, wherein said plurality of pin receiving cavities are defined as being substantially parallel to each other and extending through the pin clamping and mounting member.

3. The externally mounted, adjustable bone stabilizing frame assembly defined in claim 2, wherein each pin clamping and mounting member comprises a clamping plate receiving cavity formed therein and extending substantially perpendicular to the axis of the pin receiving cavity, whereby movement of the clamping plate in the plate receiving cavity causes frictional engagement of the clamping plate with the bone-mounted pins when said pins are positioned in the pin receiving cavity.

4. The externally mounted, adjustable bone stabilizing frame assembly defined in claim 3, wherein said pin receiving cavity comprises a cross-sectional shape selected from the group consisting of squares and rectangles, each having a plurality of adjacent surfaces, thereby enabling bone-mounted pins of different diameters to be secure therein.

5. The externally mounted, adjustable bone stabilizing frame assembly defined in claim 4, wherein the clamping plate comprises a pin engaging surface controllably moved by the wedge member for bringing the pin engaging surface into contact with the pin mounted in the receiving cavity and securely locking the pin between the engaging face of the clamping plate and the adjacent surfaces of the pin receiving cavity, whereby pins of different diameters are easily secured thereby.

6. An externally mounted, adjustable bone stabilizing frame assembly constructed for engaging and holding a plurality of bone-mounted pins in a precisely desired orientation, said frame assembly comprising:
   A. a plurality of pin clamping and mounting members constructed for being securely engaged with the bone-mounted pins and comprising at least one rod mounted thereto and extending therefrom;
   B. at least one stabilizing rod positioned in cooperating relationship with the pin clamping and mounting members, and
   C. at least two clamp assemblies positioned in a substantially stacked relationship with each clamping member comprising:
      A. a pair of clamping members incorporating an integrated, generally C-shape and comprising:
         1. a clamping zone,
         2. a first control plate and a second control plate positioned in juxtaposed, spaced, cooperating, overlying relationship, interconnected to the clamping zone, incorporating axially aligned apertures and constructed for providing a controlled clamping force to the clamping zone, and
         3. pivot means interconnected to the control plates for cooperating therewith to provide the desired arcuate pivoting movement for controlling the clamping forces of the clamping zone;
      B. control means associated with the first and second clamping plates for providing the desired clamping forces thereto, and
      C. a bushing mounted in and extending between the control plates of adjacent clamping members, thereby maintaining the clamping members in stacked vertical relationship with each other, preventing angular shifting or tilting thereof.

7. The externally mounted, adjustable bone stabilizing frame assembly defined in claim 6, wherein the second control plate of each clamping member comprises a threaded zone formed therein and the first control plates of each clamping member are mounted in stacked engagement with each other.

8. The externally mounted, adjustable bone stabilizing frame assembly defined in claim 7, wherein the control means is defined as comprising an elongated rod having a head portion formed at one end, an enlarged flange formed adjacent the head portion for contacting and engaging a surface of the second control plate of a first clamping member, a substantially smooth intermediate portion formed for telescopic insertion through apertures formed in the first and second clamping plates, and a terminated threaded surface constructed for engagement in the threaded zone of the second clamping plate, whereby rotational movement of the control means provides clamping forces to the clamp assembly.

9. The externally mounted, adjustable bone stabilizing frame assembly defined in claim 8, wherein the pivot means comprises an interconnecting wall integrally formed with and interconnected to the first and second clamping plates and a flexing zone formed adjacent the wall for controlling the movement of the control plate.

10. The externally mounted, adjustable bone stabilizing frame assembly defined in claim 9, wherein said flexing zone comprises an enlarged arcuate curved area and the pivot zone comprises a pivot pin mounted in the arcuate curved area, providing controlled flexing movement of the control plates while preventing deformation of the wall associated therewith.

11. The externally mounted, adjustable bone stabilizing frame assembly defined in claim 9, wherein said flexing zone comprises an arcuate curved recess formed between each control plate and the interconnecting wall, thereby controlling movement of the control plate and preventing deformation of the interconnecting wall.

12. The externally mounted, adjustable bone stabilizing frame assembly defined in claim 6, wherein the clamping zone is formed by a first clamping plate mounted to and extending from the first control plate and a second clamping plate mounted to and extending from the second control plate, whereby movement of the control means causes the first and second clamping late to move therewith.

13. The externally mounted, adjustable bone stabilizing frame assembly defined in claim 6, wherein the clamping zone is formed by a continuous, arcuately curved wall member extending from the first contact plate to the second contact plate, establishing a substantially circular shaped clamping zone.

14. The externally mounted, adjustable bone stabilizing frame assembly defined in claim 13, wherein said circular shaped clamping zone is further defined as comprising a friction member formed therein for retaining and frictionally molding a rod member inserted therein prior to the secure clamped engagement of the clamping zone about the rod member.

15. The externally mounted, adjustable bone stabilizing frame assembly defined in claim 14, wherein the friction member comprises an elongated threaded shaft extending through the first contact plate to the second contact plate with the outer surface thereof extending into the clamping zone for providing the desired frictional interference.

16. An externally mounted, adjustable bone stabilizing frame assembly constructed for engaging and holding a plurality of bone-mounted pins in a precisely desired orientation, said frame assembly comprising:
   A. a plurality of pin clamping and mounting members comprising:
      A. a plurality of pin receiving cavities constructed for receiving and securely clamping the bone-mounted pins therein,
      B. a clamping plate movably mounted in the pins clamping and mounting member in cooperating relationship with the pin receiving cavity,
      C. a wedge member movably mounted in the pin clamping and mounting member and controllably engaged with the clamping plate for controlling the movement thereof into engagement with the bone-mounted pins mounted in the pin receiving cavities; and
      D. at least one rod mounted to the pin clamping and mounting member and extending therefrom;
   B. at least one stabilizing rod positioned in cooperating relationship with the pin clamping and mounting members, and
   C. at least two clamp assemblies positioned in a substantially stacked relationship with each clamping member comprising:
      A. a pair of clamping members incorporating an integrated, generally C-shape and comprising:
         1. a clamping zone,
         2. a first control plate and a second control plate positioned in juxtaposed, spaced, cooperating, overlying relationship, interconnected to the clamping zone, incorporating axially aligned apertures and constructed for providing a controlled clamping force to the clamping zone, and
         3. pivot means interconnected to the control plates for cooperating therewith to provide the desired arcuate pivoting movement for controlling the clamping forces of the clamping zone;
      B. control means associated with the first and second clamping plates for providing the desired clamping forces thereto, and
      C. a bushing mounted in and extending between the control plates of adjacent clamping members, thereby maintaining the clamping members in stacked vertical relationship with each other, preventing angular shifting or tilting thereof.

17. A pin clamping and mounting member constructed for use in an externally mounted, adjustable bone stabilizing frame assembly adapted for engaging and holding a plurality of bone-mounted pins in a precisely desired orientation, said pin clamping and mounting member comprising a housing incorporating:
   A. a plurality of pin receiving cavities constructed for receiving and securely clamping the bone-mounted pins therein,
   B. a clamping plate movably mounted in the pins clamping and mounting member in cooperating relationship with the pin receiving cavity,
   C. a wedge member movably mounted in the pin clamping and mounting member and controllably engaged with the clamping plate for controlling the movement thereof into engagement with the bone-mounted pins mounted in the pin receiving cavities; and
   D. at least one rod mounted to the pin clamping and mounting member and extending therefrom.

18. A clamping assembly constructed for use in an externally mounted, adjustable bone stabilizing frame assembly adapted for engaging and holding a plurality of bone-mounted pins in a precisely desired orientation, said clamp assembly comprising:
   A. at least one clamping member incorporating an integrated, generally C-shape and comprising:
      a. a clamping zone,
      b. a first control plate and a second control plate positioned in juxtaposed, spaced, cooperating, overlying relationship, interconnected to the clamping zone, incorporating axially aligned apertures and constructed for providing a controlled clamping force to the clamping zone, and
      C. pivot means interconnected to the control plates for cooperating therewith to provide the desired arcuate pivoting movement for controlling the clamping forces of the clamping zone;
   B. control means associated with the first and second clamping plates for providing the desired clamping forces thereto, and
   C. a bushing mounted in and extending between the control plates of adjacent clamping members, thereby maintaining the clamping members in stacked vertical relationship with each other, preventing angular shifting or tilting thereof.

* * * * *